United States Patent [19]

Yoon

[11] Patent Number: 5,797,927

[45] Date of Patent: Aug. 25, 1998

[54] COMBINED TISSUE CLAMPING AND SUTURING INSTRUMENT

[76] Inventor: InBae Yoon, 2101 Highland Ridge Dr., Phoenix, Md. 21131

[21] Appl. No.: 532,461

[22] Filed: Sep. 22, 1995

[51] Int. Cl.$^6$ ..................................................... A61B 17/04
[52] U.S. Cl. ........................... 606/144; 606/139; 606/146
[58] Field of Search .......................... 606/144, 145, 606/146, 148, 147, 139, 222, 223, 224, 225

[56] References Cited

U.S. PATENT DOCUMENTS

| | | |
|---|---|---|
| 373,372 | 11/1887 | King . |
| 786,000 | 3/1905 | Botkin . |
| 919,138 | 4/1909 | Drake et al. . |
| 1,037,864 | 9/1912 | Carlson et al. . |
| 1,066,317 | 7/1913 | Pirnat . |
| 1,449,087 | 3/1923 | Bugbee . |
| 1,635,066 | 7/1927 | Wells . |
| 1,815,725 | 7/1931 | Pilling et al. . |
| 1,822,330 | 9/1931 | Ainslie . |
| 1,856,721 | 5/1932 | Nagelmann . |
| 1,933,024 | 10/1933 | Nagelmann . |
| 2,213,830 | 9/1940 | Anastasi . |
| 2,396,180 | 3/1946 | Karle . |
| 2,414,746 | 1/1947 | Karle . |
| 2,611,366 | 9/1952 | Mull . |
| 2,646,045 | 7/1953 | Priestley . |
| 2,808,055 | 10/1957 | Thayer . |
| 2,959,172 | 11/1960 | Held . |
| 3,013,559 | 12/1961 | Thomas . |
| 3,090,386 | 5/1963 | Curtis . |
| 3,249,104 | 5/1966 | Hohnstein . |
| 3,470,875 | 10/1969 | Johnson . |
| 3,638,653 | 2/1972 | Berry . |

(List continued on next page.)

FOREIGN PATENT DOCUMENTS

| | | |
|---|---|---|
| 0535906 | 7/1993 | European Pat. Off. . |
| 180125 | 7/1986 | Japan ............................................ 17/6 |

*Primary Examiner*—Michael Buiz
*Assistant Examiner*—Tina T. D. Pham

[57] ABSTRACT

A combined tissue clamping and suturing instrument includes a pair of opposed jaws selectively actuated by operation of a handle portion, a hollow suture needle mounted on a first of the jaws and provided with a slot, and a length of suture material extending through the hollow needle. A groove is preferably formed on a peripheral side wall of the first jaw so that a portion of the suture material can be disposed within the groove and, when provided, the groove preferably communicates with a first open end of the hollow suture needle. The slot and groove each have a width to prevent the suture material from inadvertently falling out while permitting deliberate removal of the suture material via the slot or groove by application of force so that suturing of anatomical tissue can be performed with tissue held between jaws of the instrument. In a preferred embodiment, an opening is formed in the second jaw in opposed relation to the hollow suture needle such that, when the jaws are closed, the hollow suture needle will protrude from the opening and suture material disposed in the needle can be grasped. In other embodiments, a plurality of solid or hollow suture needles are longitudinally and/or laterally spaced on a jaw to carry plural lengths of suture material through anatomical tissue to be sutured in a single operation. A blade can optionally be advanced along a cutting channel formed in the jaw to cut anatomical tissue between the jaws.

44 Claims, 9 Drawing Sheets

U.S. PATENT DOCUMENTS

| | | |
|---|---|---|
| 3,840,017 | 10/1974 | Violante . |
| 3,842,840 | 10/1974 | Schweizer . |
| 3,901,244 | 8/1975 | Schweizer . |
| 3,946,740 | 3/1976 | Bassett . |
| 4,064,881 | 12/1977 | Meredith . |
| 4,164,225 | 8/1979 | Johnson et al. . |
| 4,169,476 | 10/1979 | Hilterbrandt . |
| 4,224,947 | 9/1980 | Fukuda . |
| 4,312,337 | 1/1982 | Donohue . |
| 4,493,323 | 1/1985 | Albright et al. . |
| 4,596,249 | 6/1986 | Freda et al. . |
| 4,602,635 | 7/1986 | Mulhollan et al. . |
| 4,621,640 | 11/1986 | Mulhollan et al. . |
| 4,890,615 | 1/1990 | Caspari et al. . |
| 4,923,461 | 5/1990 | Caspari et al. . |
| 4,957,498 | 9/1990 | Caspari et al. . |
| 5,059,201 | 10/1991 | Asnis . |
| 5,100,421 | 3/1992 | Christoudias . |
| 5,181,919 | 1/1993 | Bergman et al. . |
| 5,254,126 | 10/1993 | Filipi . |
| 5,304,184 | 4/1994 | Hathaway et al. . |
| 5,318,577 | 6/1994 | Li . |
| 5,320,632 | 6/1994 | Heidmueller . |
| 5,336,229 | 8/1994 | Noda . |
| 5,389,103 | 2/1995 | Melzer et al. . |
| 5,397,325 | 3/1995 | Della Badia et al. . |

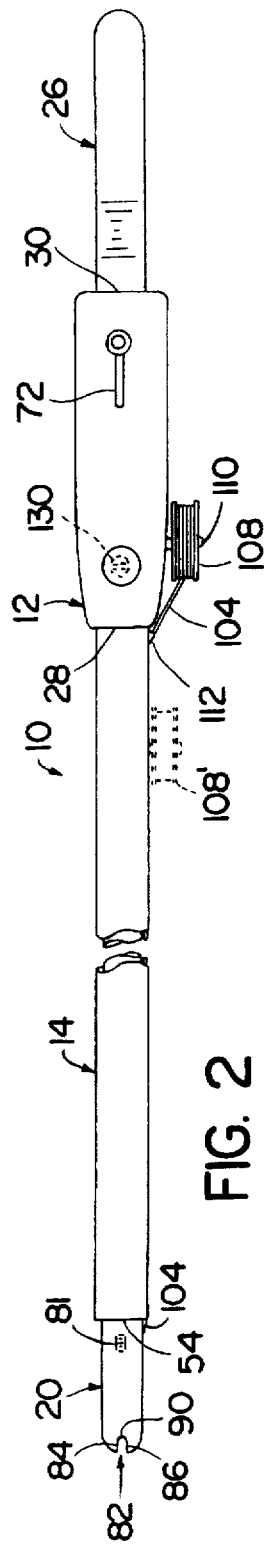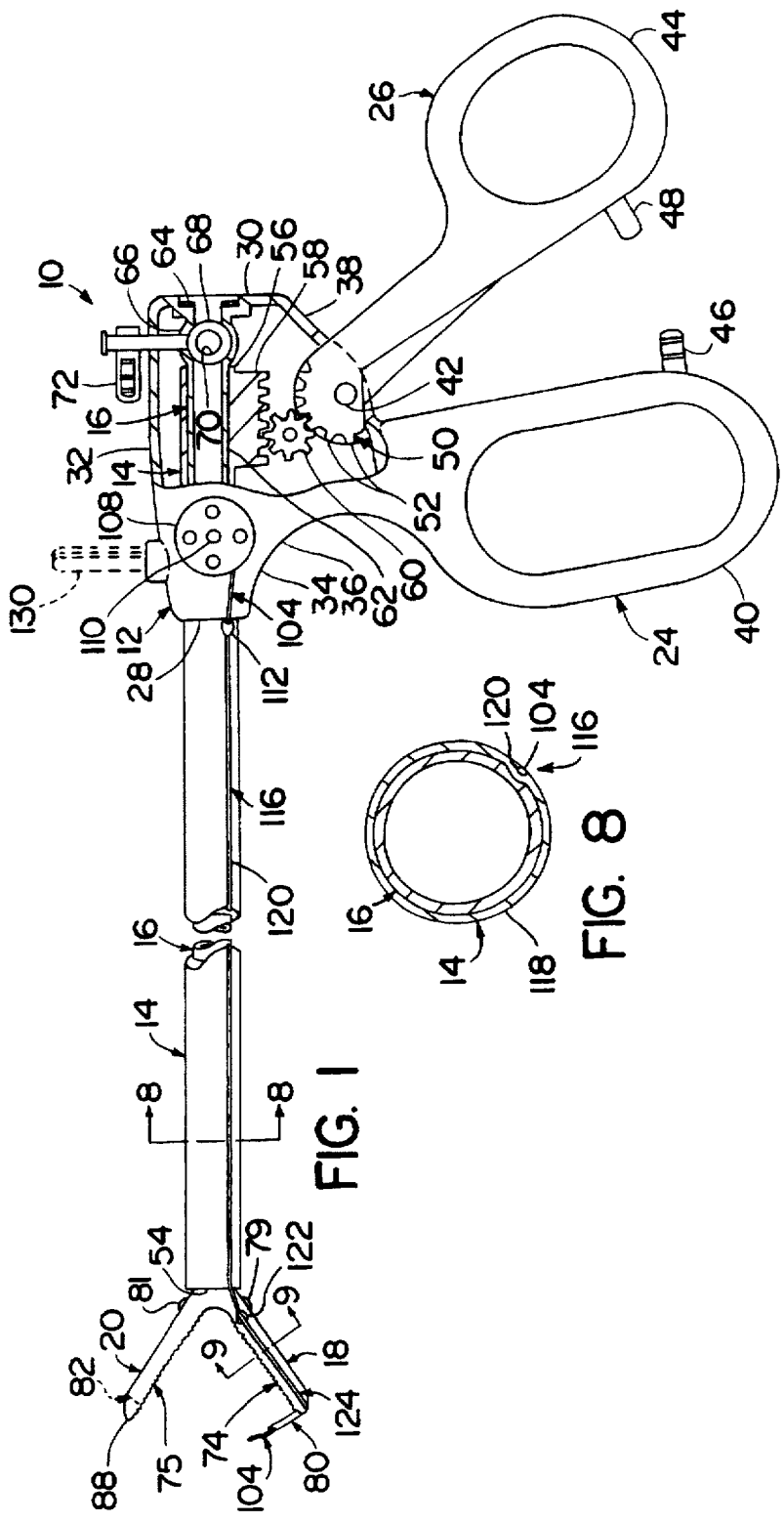

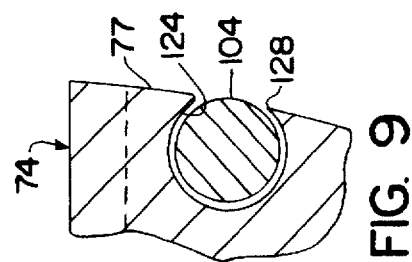
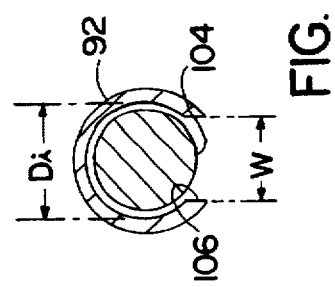
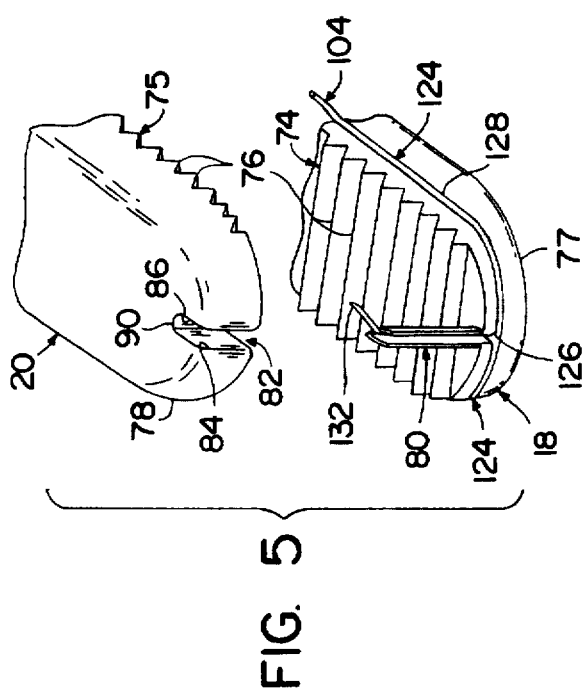
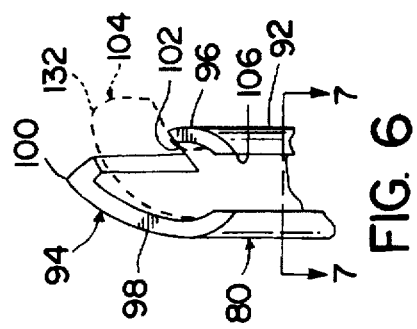

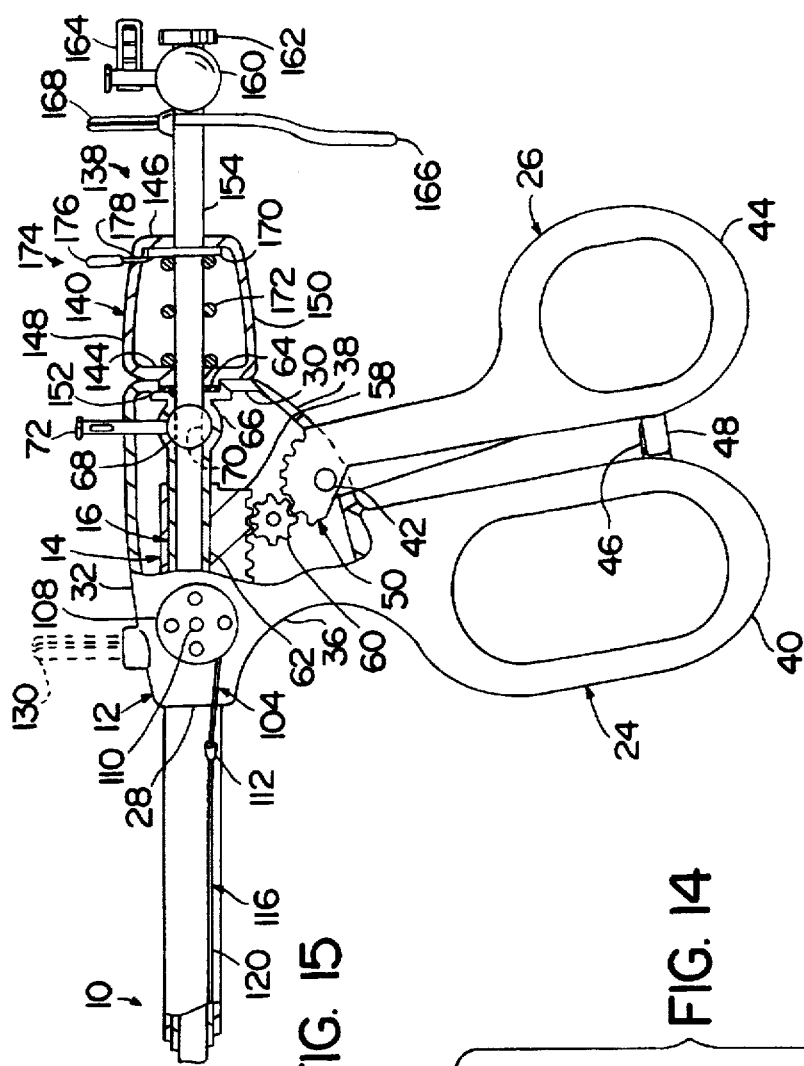
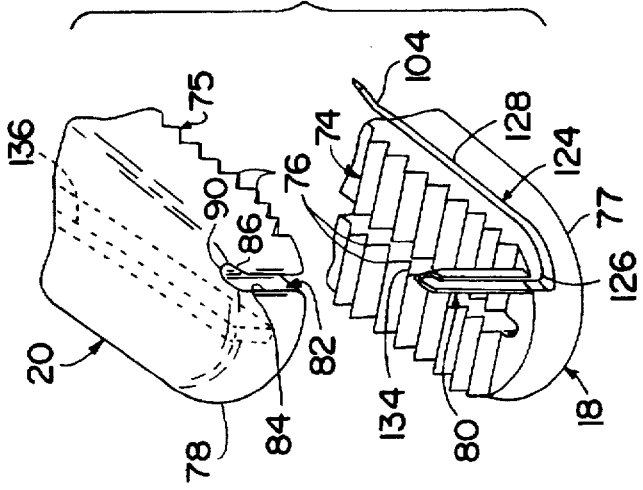

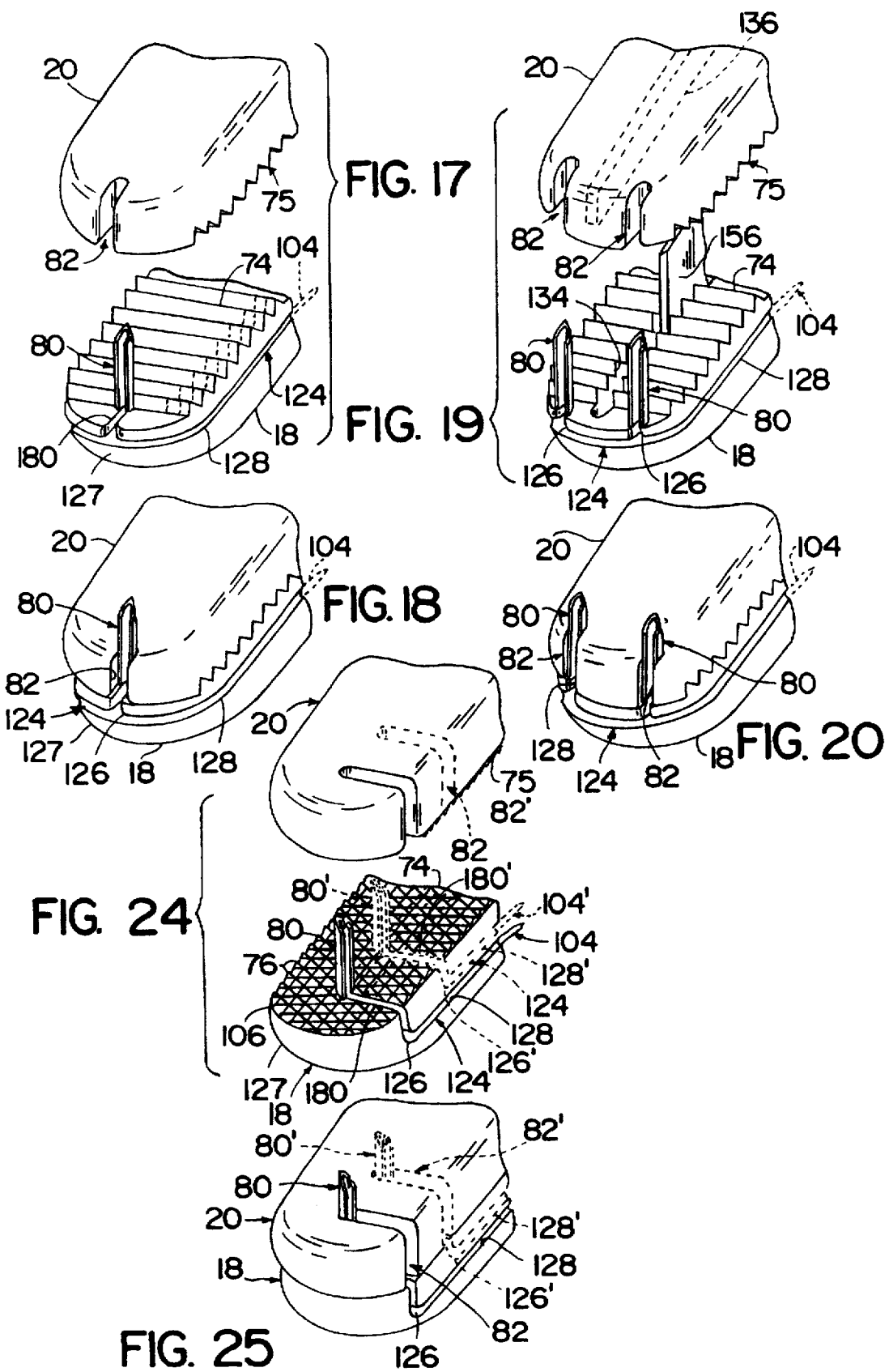

COMBINED TISSUE CLAMPING AND SUTURING INSTRUMENT

BACKGROUND OF THE INVENTION

1. Field of Invention

The present invention pertains to surgical instruments and, more particularly, to surgical instruments and methods for simultaneously clamping and suturing anatomical tissue during surgical procedures.

2. Discussion of the Prior Art

Suturing of bodily tissue, that is, the practice of using lengths of suture material to ligate or approximate tissue, is a time consuming part of most surgical procedures including both open surgery and endoscopic or closed surgery. By "open surgery" is meant surgery wherein the surgeon gains access to the surgical site by a relatively large incision, and by "endoscopic surgery" is meant minimally invasive surgery wherein the surgeon gains access to the surgical site via one or more portals through which endoscopes are introduced to view the surgical site and through which instruments, such as forceps, cutters, applicators and the like, are introduced to the surgical site.

In the past, suturing has been accomplished with the use of a sharp suture needle carrying a length of suture material, the suture needle being caused to penetrate and pass through the tissue pulling the suture material through the tissue. Once the suture material has been pulled through the tissue, the surgeon ties a knot in the suture material, the knotting procedure allowing the surgeon to adjust the tension on the suture material to accommodate the particular tissue being sutured and control approximation, occlusion, attachment or other conditions of the tissue.

Conventional suturing with a suture needle and a length of suture material is often used in combination with clamping to control bleeding when anatomical tissue is to be cut or divided as part of the surgical procedure. Ordinarily, one or more clamps are applied to the tissue alongside the cutting line to control bleeding by compressing the clamped portion of the tissue. Once clamped, the tissue is cut using a cutting instrument such as a scissors or knife, and a suture needle carrying a length of suture material is grasped by hand or using a needle holder and is moved into the body. The needle is caused to penetrate and pass through the tissue adjacent the clamp until the point of the needle is observed to emerge from the opposite side of the tissue. The point of the needle is grasped as it emerges and is pulled away from the tissue to draw the suture material through the tissue. When a suitable length of suture material has been drawn through the tissue, the surgeon forms a ligature around the divided tissue adjacent the cut.

When suturing anatomical tissue, it is important that the point of the needle be precisely aligned with the tip of the clamping instrument prior to being forced through the tissue. When surgery is to be performed in awkward and restricted spaces, it is difficult to position the needle adjacent the tip of the clamping instrument since there is little room for maneuvering instruments and a greater chance of visual obstruction. It is therefore desirable to avoid the use of multiple instruments for tissue clamping and suturing, particularly in certain relatively inaccessible anatomical spaces.

U.S. Pat. No. 2,213,830 to Anastasi discloses a suturing and ligating instrument having a pair of gripping levers pivotally connected with a needle operating lever, one of the gripping levers pivotally mounting a curved needle and the other gripping lever being bifurcated to receive the needle between branches of the bifurcation. A length of suture material is attached to the needle via an eye formed near the point of the needle and is disposed alongside the needle during operation of the instrument. The needle operating lever is biased away from the gripping lever carrying the needle such that, in a normally open condition, the needle operating lever pivots the needle outwardly of the gripping lever via a stop acting on an inner concave surface of the needle. In a closed condition, the needle operating lever pivots the needle through both gripping levers and any tissue held therebetween. The suture material is carried alongside the needle as it is swung through the tissue and, as a result of the added bulk, this type of instrument is likely to create a larger hole than the size of the needle or suture material with additional trauma to the tissue.

U.S. Pat. No. 3,470,875 to Johnson describes a surgical clamping and suturing instrument having pivotally interconnected arms with one or more apertures being formed at the outer end of one of the arms for receiving and gripping a needle and a capsule containing a suture with one or more needles connected thereto being removably mounted at the outer end of the opposed arm. Upon closing of the arms, the needles are transferred from the capsule to the receiving apertures, carrying a length of suture material with them. A disadvantage of this type of device is that the arms must be opened in order to grasp the length of suture material extending through the tissue; and, accordingly, it is not possible to tie a ligature or stitch while simultaneously releasing clamping pressure on the tissue.

U.S. Pat. No. 4,596,249 to Freda et al discloses an instrument for setting sutures having a pair of pivotally connected arms, one of the arms forming a jaw with a tissue piercing hook and the other arm forming a jaw with a notch or opening for receiving the hook. A length of suture material extends across the notch or opening in opposed relation to the tissue piercing hook and is caught by an inner concave surface of the hook when the hook penetrates through anatomical tissue and is subsequently withdrawn. The hook is generally triangular in shape with a broad base and a pointed or sharpened end, the size of the hook being sufficiently large to form a concave inner surface suitable for catching the suture material as it is withdrawn from the opening in the opposed jaw and, consequently, causing additional trauma to the tissue.

The foregoing instruments each include pivotally connected arms that expand laterally when opened. Consequently, although these instruments are appropriate for use in open surgery, such instruments are unsuitable for use in endoscopic or minimally invasive surgery since they cannot be introduced through an incision or portal in the body.

U.S. Pat. No. 4,957,498 to Caspari et al discloses a suturing instrument for use in arthroscopic surgery including a tubular shaft having a jaw assembly at the distal end thereof. A hollow, curved needle is affixed to the lower jaw in opposed relation to an aperture formed in the upper jaw, and a length of suture material, originating from a spool mechanism positioned at the proximal end of the tubular shaft, is passed through the shaft and extends longitudinally through the needle. In operation, upper and lower jaws of the instrument locally clamp a small amount of tissue adjacent the needle allowing the needle to punch through the tissue when the jaws are closed. Suture material is then fed through the needle until it extends out of the needle and the jaws of the instrument are opened to withdraw the needle back through the tissue and free ends of the suture material are drawn out of the body with the jaws. Related disadvantages of this type of instrument are that the jaws are of insufficient size to clamp broad segments of tissue and that the jaws must be opened to obtain access to the suture material when forming a suture; and, accordingly, it is not possible to form the suture while simultaneously releasing clamping pressure.

U.S. Pat. No. 5,397,325 go Della Badia et al discloses a laparoscopic suturing instrument having a tubular elongated shaft terminating in a jaw assembly at the distal end thereof, the jaw assembly including a first jaw member with a cupped recess having a wheel assembly disposed therein. The wheel assembly includes a needle mount for retaining a needle and is configured such that the needle lies within the cupped recess when the jaw members are closed and can be deployed in a protracted position away from the first jaw member when the jaw assembly is open. In operation, when the upper jaw member is closed upon the lower jaw member with the needle deployed, the needle is forced through the tissue positioned between the jaws. A clamping member is then used to grasp the needle, thereby releasing the needle from the needle mount, and the needle and suturing thread are pulled through the tissue and withdrawn from the body to tie an extracorporeal knot. A disadvantage of this type of instrument is that the needle must be removed from the jaws in order to release the suture material from the instrument, thereby necessitating additional instruments such as needle holders and increasing the likelihood of sharp needles being dropped within the body.

SUMMARY OF THE INVENTION

Accordingly, it is a primary object of the present invention to provide a combined tissue clamping and suturing instrument overcoming the above-mentioned disadvantages of the prior art.

Another object of the present invention is to permit various types of sutures to be formed without the need of having to use multiple tissue clamping and needle holding instruments.

A further object of the present invention is to facilitate accurate placement of a needle adjacent clamped anatomical tissue for suturing without the need of having to directly visually observe the needle.

An additional object of the present invention is to permit easy removal of a length of suture material from a needle mounted on the jaw of a combined tissue clamping and suturing instrument without opening the jaws of the instrument such that suturing can be performed substantially simultaneously with removal of the clamping pressure.

The present invention has another object in minimizing penetration resistance of a suture needle mounted on a jaw of a combined tissue clamping and suturing instrument in order to reduce tissue trauma.

Still another object of the present invention is to permit anatomical tissue to be clamped, cut and sutured without the need of having to use separate tissue clamping, needle holding and cutting instruments.

Yet a further object of the present invention is to facilitate placement of a suture immediately adjacent a cut edge of anatomical tissue in order to minimize the amount of tissue overhanging the suture.

It is an additional object of the present invention to permit multiple lengths of suture material to be placed in anatomical tissue simultaneously with clamping of the tissue.

The present invention is generally characterized in a surgical instrument including a pair of opposed jaws selectively actuated by operation of a handle portion, a hollow suture needle mounted on a first of the jaws and provided with a slot, and a length of suture material extending through the hollow needle. The hollow needle has a first open end mounted on the first jaw and a second open end defining a tissue penetrating point, the first and second open ends being connected by the slot. A groove is preferably formed on an outer surface of the first jaw so that a portion of the suture material can be disposed within the groove and, when provided, the groove preferably communicates with the first open end of the hollow suture needle. The slot and groove each have a width to prevent the suture material from inadvertently falling out while permitting deliberate removal of the suture material via the slot and/or groove by application of force so that suturing of anatomical tissue can be performed with tissue held between jaws of the instrument. In a preferred embodiment, an opening is formed in the second jaw in opposed relation to the hollow suture needle such that, when the jaws are closed, the hollow suture needle will protrude from the opening and suture material disposed in the needle can be grasped and removed from the instrument.

Another aspect of the present invention is generally characterized in a surgical instrument including a pair of opposed jaws selectively actuated by operation of a handle portion, a longitudinal cutting channel formed in a first of the jaws, a cutting member movable along the longitudinal cutting channel, a suture needle extending from the first jaw to a tissue penetrating point and a length of suture material attached to the suture needle near the tissue penetrating point.

A further aspect of the present invention is generally characterized in a surgical instrument including a pair of opposed jaws selectively actuated by operation of a handle portion, a plurality of longitudinally spaced suture needles, each of the needles extending from a first one of the jaws to a tissue penetrating point, and plural lengths of suture material, each of the lengths being attached to one of the suture needles near a respective tissue penetrating point.

An additional aspect of the present invention is generally characterized in a surgical instrument including a pair of opposed jaws selectively actuated by operation of a handle portion, a plurality of laterally spaced suture needles, each of the needles extending from a first one of the jaws to a tissue penetrating point, and plural lengths of suture material, each of the lengths being attached to one of the suture needles near a respective tissue penetrating point.

Yet another aspect of the present invention is generally characterized in a method of suturing anatomical tissue using a surgical instrument having a hollow, slotted suture needle mounted on one of a pair of opposed jaws, the method including the steps of positioning a length of suture material within the suture needle, attaching the length of suture material to the suture needle near a tissue penetrating point of the suture needle, positioning the jaws around anatomical tissue to be sutured, closing the jaws to clamp the anatomical tissue between tissue clamping surfaces of the jaws, receiving the point of the suture needle within an opening formed in the opposed jaw, removing the length of suture material from within the suture needle using the slot, and forming a suture using the length of suture material while simultaneously releasing the anatomical tissue from between the opposed jaws.

Still a further aspect of the present invention is generally characterized in a method of suturing anatomical tissue using a surgical instrument having a suture needle mounted on one of a pair of opposed jaws, the method including the steps of attaching the length of suture material to the suture needle near a tissue penetrating point of the suture needle, positioning the jaws around anatomical tissue to be sutured, closing the jaws to clamp the anatomical tissue between tissue clamping surfaces of the jaws, receiving the point of the suture needle within an opening formed in the opposed jaw, advancing a blade along a channel formed in at least one of the jaws to cut the anatomical tissue clamped between the jaws, removing the length of suture material from the suture needle, and forming a suture using the length of suture material while simultaneously releasing the anatomical tissue from between the opposed jaws.

Another aspect of the present invention is generally characterized in a method of suturing anatomical tissue using a surgical instrument having a pair of laterally spaced suture needles mounted on one of a pair of opposed jaws, the method including the steps of attaching lengths of suture material to the pair of laterally spaced suture needles, positioning the jaws around anatomical tissue to be sutured, closing the jaws to clamp the anatomical tissue between tissue clamping surfaces of the jaws, penetrating through the anatomical tissue using the pair of laterally spaced suture needles, receiving points of the suture needles within openings formed in the opposed jaw, removing the lengths of suture material from the suture needles, and forming sutures using the lengths of suture material while simultaneously releasing the anatomical tissue from between the opposed jaws.

Yet another aspect of the present invention is generally characterized in a method of suturing anatomical tissue using a surgical instrument having a plurality of longitudinally spaced suture needles mounted on one of a pair of opposed jaws, the method including the steps of attaching lengths of suture material to the longitudinally spaced suture needles, positioning the jaws around anatomical tissue to be sutured, closing the jaws to clamp the anatomical tissue between tissue clamping surfaces of the jaws, penetrating through the anatomical tissue using the longitudinally spaced suture needles, receiving points of the suture needles within openings formed in the opposed jaw, removing the lengths of suture material from the suture needles, and forming sutures using the lengths of suture material while simultaneously releasing the anatomical tissue from between the opposed jaws.

Other objects and advantages of the present invention will become apparent from the following description of the preferred embodiments taken in conjunction with the accompanying drawings, wherein like parts in each of the several figures are identified by the same reference characters.

BRIEF DESCRIPTION OF THE DRAWINGS

FIG. 1 is a broken side view, in elevation, of the combined tissue clamping and suturing instrument of the present invention in an open position.

FIG. 2 is a broken top view, in plan, of the combined tissue clamping and suturing instrument of FIG. 1.

FIG. 5 is a fragmentary view, in perspective, of the jaws of the combined tissue clamping and suturing instrument of FIG. 1 in the open position.

FIG. 6 is a fragmentary front view of a suture needle mounted on one of the jaws of the combined tissue clamping and suturing instrument of FIG. 1.

FIG. 7 is a sectional view of the suture needle and a length of suture material taken along line 7—7 in FIG. 6.

FIG. 8 is a sectional view of outer and intermediate members of the combined tissue clamping and suturing instrument taken along line 8—8 in FIG. 1.

FIG. 9 is a fragmentary sectional view of a groove formed in a jaw of the combined tissue clamping and suturing instrument taken along line 9—9 in FIG. 1.

FIG. 14 is a fragmentary perspective view of a modification of the combined tissue clamping and suturing instrument according to the present invention.

FIG. 15 is a broken side view, in elevation, showing the combined tissue clamping and suturing instrument of FIG. 14 coupled with an operating unit carrying a cutting member.

FIGS. 17 and 18 are fragmentary perspective views of a modification of the combined tissue clamping and suturing instrument according to the present invention.

FIGS. 19 and 20 are fragmentary perspective views of another modification of the combined tissue clamping and suturing instrument according to the present invention.

FIGS. 24 and 25 are fragmentary perspective views of still another modification of the combined tissue clamping and suturing instrument according to the present invention.

DESCRIPTION OF THE PREFERRED EMBODIMENTS

Figure 3:
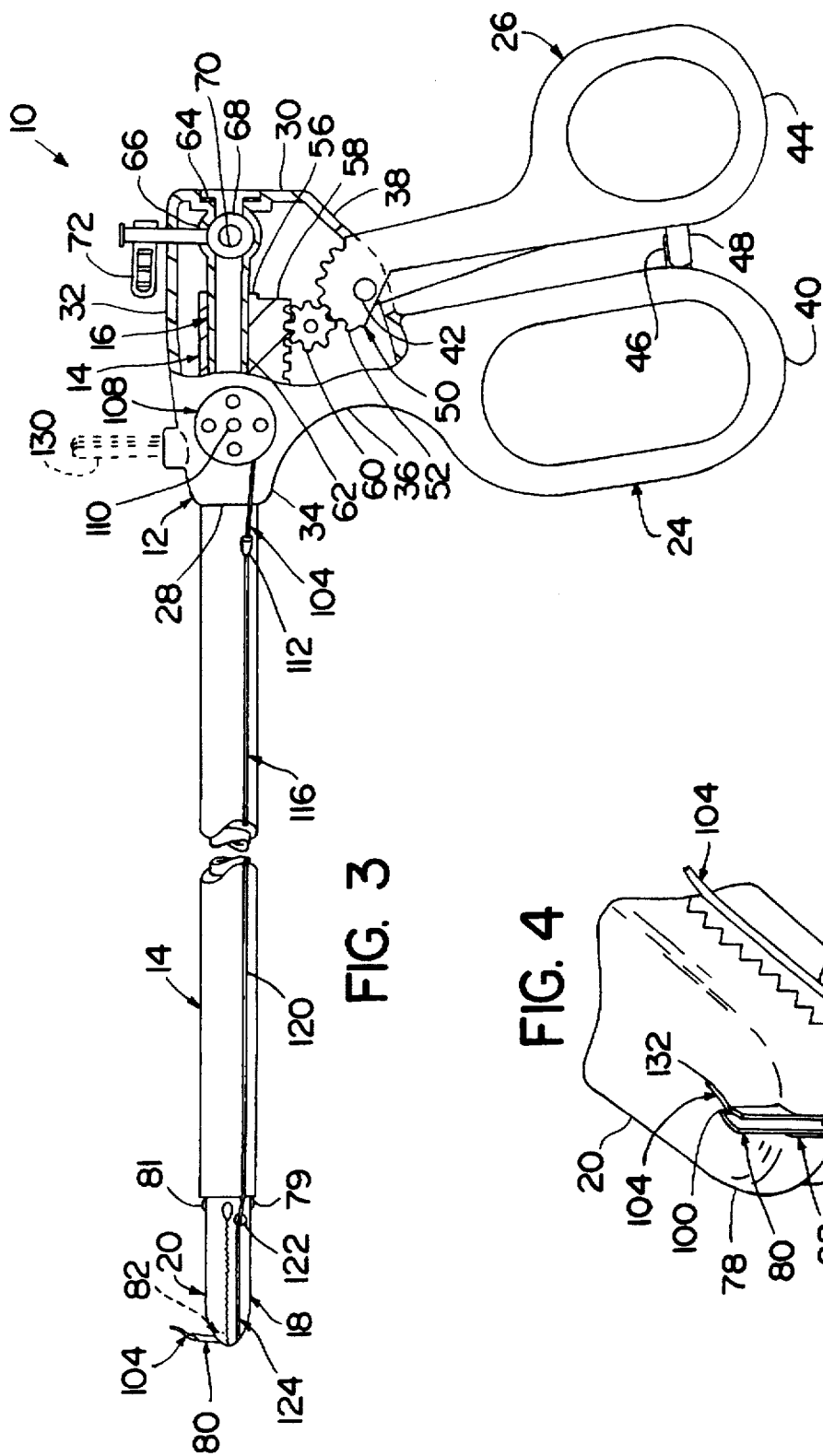
FIG. 3 is a broken side view, in elevation, of the combined tissue clamping and suturing instrument of FIG. 1 in a closed position.

The surgical instrument of the present invention can be utilized to clamp and suture any type of anatomical tissue in any type of anatomical cavity; and, accordingly, while the instrument is described hereinafter for use with a portal sleeve in endoscopic procedures, such as laparoscopy, the instrument can be used in open surgery and with catheters and other small and large diameter cylindrical members providing access to small cavities, such as veins and arteries, as well as large cavities, such as the abdomen.

A combined tissue clamping and suturing instrument 10 in accordance with the present invention, as illustrated in FIGS. 1 and 2, includes a housing 12, an outer tubular member 14 extending distally from the housing 12, an intermediate tubular member 16 telescopically fitted within the outer tubular member 14 and terminating distally in a pair of opposed jaws 18 and 20, and a handle portion formed of a fixed handle 24 and a movable handle 26.

Housing 12 includes longitudinally spaced front and rear walls 28 and 30 oriented perpendicular to a longitudinal axis of the instrument, a top wall 32 substantially parallel to the longitudinal axis, and a bottom wall 34 having a concave forward portion 36 curving downward from the front wall to connect with an upper end of fixed handle 24 and a rearward portion 38 extending proximally at an angle relative to the longitudinal axis of the instrument from an upper end of the handle 24 to rear wall 30. A lower end of the fixed handle 24 is configured as an elongate finger loop 40 to accommodate one or more fingers of a user. Movable handle 26 is pivotally mounted on a pin 42 proximally spaced from fixed handle 24 and secured internally to a wall or walls of the housing. A lower end of the handle 26 is configured as a finger loop 44 to accommodate one or more fingers of the user, and a pair of mating protrusions 46 and 48 are carried in opposed relation on finger loops 40 and 44 for ratchet-like engagement during operational use. Handle 26 includes an arcuate end portion 50 disposed within the housing 12 and defining a plurality of gear teeth 52 on a side of the pin 42 opposite finger loop 44.

Outer tubular member 14 is open at both ends and extends distally from housing 12 through an opening in the front wall 28 of the housing. Distal end 54 of outer tubular member 14 can be blunt as shown, tapered, beveled, slotted or chamfered as desired or have any other suitable distal configuration. Preferably, outer tubular member 14 is made of a substantially cylindrical length of a substantially rigid material, such as stainless steel or other medically acceptable plastic or metal material. A proximal end 56 of the outer tubular member is movably disposed within the housing and carries a rack 58 in spaced relation to the toothed end portion 50 of handle 26. A pinion gear 60 is meshed between the rack 58 and toothed end portion 50 of the handle to convert rotary or pivotal movement of the handle into linear movement of the rack. Looking at FIGS. 1 and 3, it will be appreciated that counterclockwise rotation of handle 26 about pin 42 results in proximal movement of outer tubular member 14 relative to the housing and that clockwise rotation of the handle 26 about pin 42 results in distal movement of the outer tubular member relative to the housing. In a preferred embodiment, movable handle 26 is biased in a clockwise direction toward fixed handle 24, for example by use of a torsion spring (not shown) coiled around pin 42 and connected between the movable handle and the fixed handle and/or the housing.

Intermediate member 16 includes a tubular portion 62 telescopically fitted within the outer tubular member 14. A proximal end of the intermediate member is fixed to the rear wall 30 of the housing and configured to form a cylindrical recess 64 in the rear wall for coupling operating units, medical instruments and accessories with the instrument and a spherical valve housing 66 distally spaced from the recess. A spherical valve member 68 with a cylindrical aperture or passage 70 formed therethrough is rotatably disposed within the valve housing 66 and connected with a knob 72 externally of the housing for operation of the valve. The distal end of tubular portion 62 is bifurcated or split longitudinally to form integral one-piece jaws 18 and 20 in opposed relation, the jaws being normally biased apart as shown. As best seen in FIGS. 1 and 5, jaws 18 and 20 include inner, tissue-clamping surfaces 74 and 75 formed of longitudinally spaced ribs or teeth 76 and outer, peripheral surfaces 77 and 78, respectively. Wedge-like cams 79 and 81 are formed on respective outer surfaces of jaws 18 and 20 and are distally spaced from outer member distal end 54 when jaws 18 and 20 are open as shown in FIG. 1. Cams 79 and 81 taper radially inward in the direction of outer tubular member 14.

Tubular body 62 of the intermediate member is preferably formed with jaws 18 and 20 as a single unitary part using a resilient medically-acceptable material such as a spring steel or plastic having suitable elastic properties for normally biasing the upper and lower jaws 18 and 20 apart while permitting the jaws to be moved towards one another in response to axial forces acting on the jaws and/or cams as a result of relative movement between the outer tubular member 14 and intermediate member 16.

Figure 4:
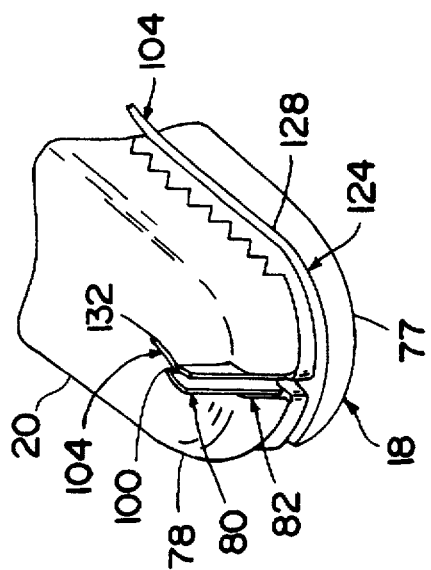
FIG. 4 is a fragmentary view, in perspective, of the jaws of the combined tissue clamping and suturing instrument of FIG. 1 in the closed position.

Referring again to FIGS. 1 and 2, a suture needle 80 is mounted on jaw 18 in opposed relation to an opening 82 formed through jaw 20, the opening being slotted or generally U-shaped with longitudinal edges 84 and 86 extending in parallel with a longitudinal axis of the instrument from a distal end or tip 88 of jaw 20 to a curved proximal edge 90 of the opening. As shown in FIGS. 3 and 4, the slotted opening 82 A aligned with needle 80 such that, when the jaws are closed, the needle will extend into the slotted opening.

Suture needle 80 includes a hollow, tubular body 92, as shown in FIGS. 5–7, extending substantially transversely from clamping surface 74 to a beveled end 94 where peripheral edges 96 and 98 of the needle converge to form a tip or point 100 for penetrating anatomical tissue to be sutured, a notch 102 being formed along peripheral edge 96 adjacent point 100 for attaching a length of suture material 104 to the needle. Tubular needle body 92 can be straight or curved and is preferably of circular cross-section, with an inner diameter $D_i$ of the tubular body being the same as or slightly larger than the diameter of the suture material 104 and a length of the body being such that, when the jaws are closed, the tip or point of the needle will protrude through the opening formed in the opposed jaw and extend beyond the outer surface 78 of the opposed jaw. A slot 106 having a width W smaller than the diameter of suture material 104 is formed in tubular needle body 92 on a side of the needle body opposite point 100 such that both the slotted opening 82 formed in jaw 20 and the slot 106 formed in needle 80 will face distally.

Referring again to FIGS. 1 and 2, suture material 104 is shown extending from a spool 108 rotatably mounted on a pin 110 secured to housing 12, the spool being freely rotatable about the pin or ratcheted for controlled delivery of the suture material. The suture material extends distally from spool 108 into a tubular guide member 112 mounted on the exterior of outer tubular member 14 distally of housing front wall 28. The tubular guide member communicates with a groove 116 formed along the outer surface 118 of the outer tubular member, the groove 116 extending distally from the guide member to the distal end 54 of the outer tubular member. An outermost edge of groove 116 intersects the outer surface 118 of the outer tubular member to define an elongate slot 120, the groove being of circular cross-section like needle 80 with a diameter similar to or larger than the diameter of the suture material and greater than the width of slot 120 to prevent suture material from falling out of the groove. From the distal end of groove 116, the suture material extends into a funnel-shaped opening 122 formed in the outer surface 77 of jaw 18 in communication with a groove 124 formed along the jaw from the funnel-shaped opening to a bend 126 at the distal end or tip 127 of the jaw where the groove turns upward, looking at FIG. 5, to communicate with the interior of tubular needle body 92. Suture material 104 extends through the groove and the needle and is attached at the beveled end or tip of the needle via the notch 102. Groove 124 intersects the outer surface of the jaw as shown in FIG. 9 to define an elongate slot 128, the groove being of circular cross-section like needle 80 with a diameter greater than the width of slot 128 such that suture material disposed within the groove will be held therein and prevented from inadvertently falling out while at the same time being able to be deliberately pulled through the slot formed by the groove by application of force transverse to the longitudinal axis of the groove.

An insulated connector, shown by dotted lines at 130 in FIGS. 1 and 2, can optionally be mounted on housing 12 opposite the handle portion or anywhere else on the instrument to connect with electrically conductive elements of the instrument for performing unipolar or bipolar electric coagulation, for example using one or both of the jaws as conductive elements.

In use, a length of suture material 104 is fed from spool 108 through tubular guide member 112 and groove 116 into the funnel-shaped opening 122 formed in the outer surface of jaw 18 and is advanced through groove 124 into needle 80, for example, by manually rotating the spool or grasping the suture material near the spool or the distal end of the outer tubular member with a forceps or gloved fingers, pushing the suture material forward, and releasing the suture material when the grasped portion nears the tubular guide member or opening, the above steps being repeated until a distal end 132 of the suture material protrudes from the beveled end of the needle. The portion of the suture material protruding from the needle is then grasped, draped over notch 102 and pulled downward to cause the suture material to become wedged into the notch as shown in FIG. 5.

Once suture material 104 has been attached to the needle 80, instrument 10 can be grasped using finger loops 40 and 44 and guided directly to the operative site in the case of open surgery, or via a portal sleeve positioned in the wall of an anatomical cavity in the case of endoscopic or closed surgery. When passed through portal sleeves larger than the elongate tubular portion of the instrument, jaws 18 and 20 can be opened somewhat so that the point of the needle is disposed within the opening formed in the opposed jaw and thus protected. When passed through portal sleeves about the same size as the elongate tubular portion of the instrument, jaws 18 and 20 must be substantially closed, so it is preferred for the needle to be retracted, pivoted or otherwise deflected in a manner to prevent the point of the needle from protruding beyond the outer surface of the opposed jaw. If retracted, slot 106 in the needle should be aligned with a slit formed in jaw 18 to permit suture material 104 to extend into the needle when the needle is retracted.

The portal sleeve can be positioned in the anatomical cavity wall using any suitable penetrating technique, including those creating puncture sites by means of removable obturators such as trocars, and can include a valve housing, if desired, to prevent loss of pneumoperitoneum during insertion and withdrawal of the instrument 10. Visualization of the endoscopic procedure can be accomplished using a conventional endoscope incorporated into the instrument 10, for example within the central channel defined by tubular shaft 62, or separately positioned within the anatomical cavity through a second portal sleeve located at another puncture site.

The instrument 10 is advanced distally through the portal sleeve until jaws 18 and 20 emerge into the anatomical cavity. At this point jaws 18 and 20 can be opened and moved to the anatomical tissue to be sutured. Since intermediate member 16 is fixed, actuation of the jaws to open or close is controlled by moving outer tubular member 14 relative to the intermediate member. If closed, jaws 18 and 20 can be opened by moving outer tubular member 14 proximally relative to intermediate member 16. Movement of the outer tubular member over the intermediate member is controlled by operation of movable handle 26. Counterclockwise rotation of handle 26 about pin 42 results in clockwise rotation of pinion 60 which engages the gear teeth of rack 58 to cause proximal movement of the outer tubular member 14 relative to jaws 18 and 20 thereby permitting the jaws to open. Conversely, clockwise rotation of the handle 26 about pin 42 results in counterclockwise rotation of pinion 60 which engages rack 58 to cause distal movement of the outer tubular member relative to the jaws causing the jaws to close.

Movable handle 26 is preferably proximally spaced from fixed handle 24 as shown so that the user can maintain one or more fingers on the stationary handle 24 while operating the movable handle 26 with the thumb and/or other fingers of the hand. Movable handle 26 is preferably biased toward stationary handle 24 so that when the movable handle is released, for example to operate the handle of an operating unit inserted through the central channel defined by the tubular portion of the intermediate member, outer tubular member 14 will be moved over jaws 18 and 20 to close the jaws together.

Figure 10:
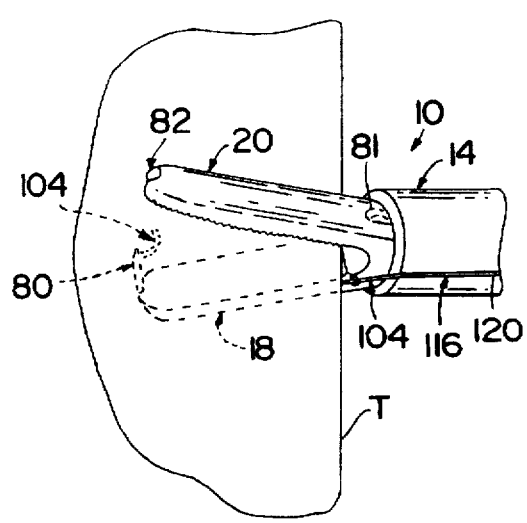
FIGS. 10–13 are fragmentary perspective views illustrating use of the combined tissue clamping and suturing instrument of FIG. 1 for tissue clamping and suturing.
Figure 11:
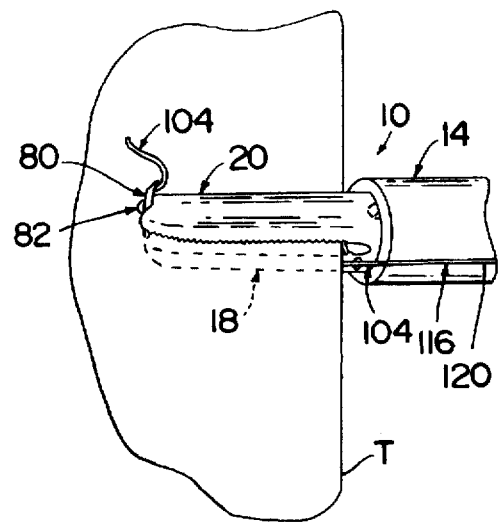

When anatomical tissue T is to be sutured (e.g., following dissection or division), jaws 18 and 20 are positioned on opposite sides of the tissue with needle 80 disposed immediately beyond the portion of the tissue to be clamped as shown in FIG. 10. Tissue T is then clamped between the jaws by squeezing finger loops 40 and 44 together to cause the tissue clamping surfaces 74 and 75 of the jaws to engage the tissue. At the same time, mating protrusions 46 and 48 engage one another to lock the jaws in the closed, clamping position shown in FIG. 11, and needle 80 is made to pass through the tissue and into slotted opening 82 carrying suture material 104.

Figure 12:
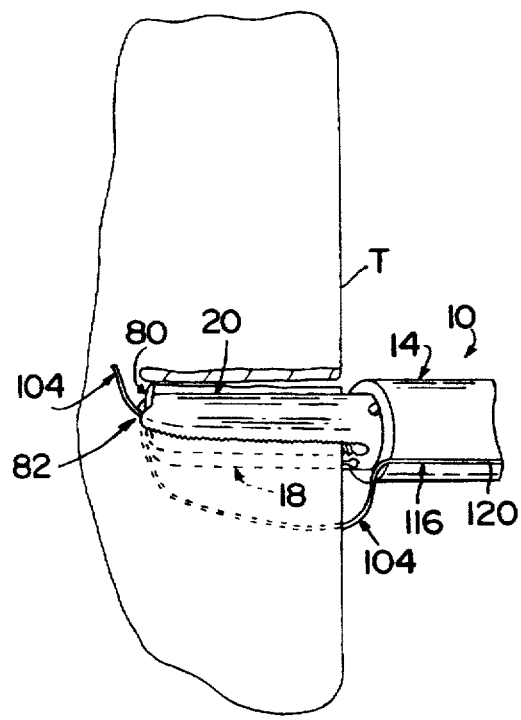

With tissue T clamped between jaws 18 and 20, a cut is made through the tissue on one side of the instrument adjacent the jaws, e.g., using a surgical scissors, and the portion of the suture material protruding from the needle is grasped and pulled away from notch 102 to release the suture material from the beveled end of the needle. Suture material 104 is also grasped near the distal end 54 of the outer tubular member and can be pulled from either grasped end, if necessary, to increase the length of suture material available for tieing-off or ligating the tissue. When a suitable length of suture material is obtained, the suture material is cut near the distal end of the outer tubular member and opposite ends of the suture material are tugged sideways, in a transverse direction relative to longitudinal axes of the needle and groove, to force the suture material through slots 106 and 128 in the needle 80 and jaw 18, respectively, such that the suture material will be released from the instrument and disposed alongside jaws 18 and 20 on the side of the instrument opposite the cut as shown in FIG. 12.

Figure 13:
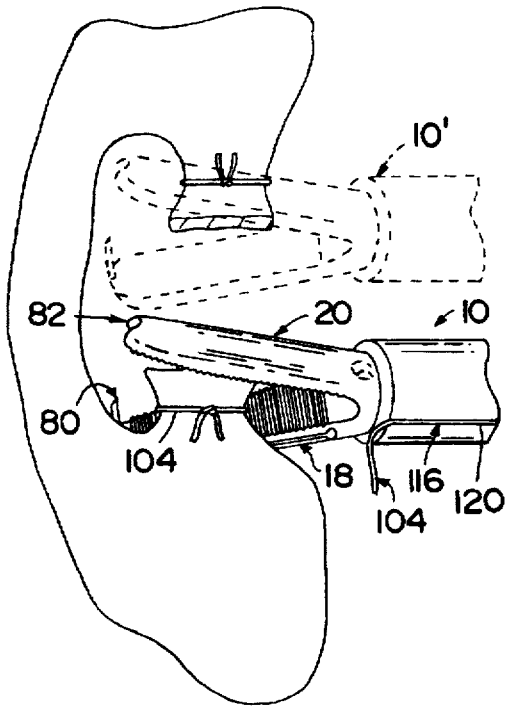

Once released from the instrument, suture material 104 can be tied around tissue T immediately adjacent jaws 18 and 20 in any conventional manner while simultaneously opening the jaws to reduce the clamping pressure applied to the tissue as shown in FIG. 13. If it is desired to prevent bleeding from both sides of the cut, a similar procedure can be performed on the other side of the cut using a second combined tissue clamping and suturing instrument 10' as shown by dotted line in FIG. 13. Instrument 10 is then moved away from the sutured tissue and is threaded in the manner described above for use at another location.

From the above, it will be appreciated that the combined tissue clamping and suturing instrument 10 of the present invention can be used anywhere in the body to form ligatures or ties around anatomical tissue using lengths of suture material carried by the instrument. The suturing instrument can, however, also be used to place stitches through anatomical tissue by positioning the tips of jaws 18 and 20 on opposite sides of the anatomical tissue to be sutured and closing the jaws in the manner described above to cause needle 80 carried by jaw 18 to penetrate through the anatomical tissue into the slotted opening formed in jaw 20. Suture material 104 carried at the beveled end of needle 80 is pulled through the anatomical tissue with the needle when the jaws are closed and can be released from the suturing instrument in the manner described above to be knotted in any conventional way or to be used in manipulating the anatomical tissue.

By mounting a hollow, slotted suture needle on a jaw and attaching suture material to the needle mounted on the jaw, the suturing instrument of the present invention permits various types of sutures to be formed without the need of having to use multiple tissue clamping and needle holding instruments. Furthermore, since the needle is fixed at a predetermined location on the jaw opposite the slotted opening, it is possible to accurately position the needle adjacent anatomical tissue to be sutured without directly visually observing the needle. In the case of a needle being mounted at the tip of a jaw, positioning the tip of the jaw at a desired suturing location will also cause the needle to be properly positioned.

A modification of the instrument 10, shown in FIGS. 14 and 15, includes a pair of cutting channels 134 and 136 formed along inner surfaces 74 and 75 of jaws 18 and 20, respectively, to permit anatomical tissue to be clamped, cut and sutured without the need of having to use separate tissue clamping, cutting and needle holding instruments. Cutting channel 134 in jaw 18 is aligned with a longitudinal axis of jaw 18 and extends from a proximal end of inner surface 74 to suture needle 89, the suture needle being slightly laterally offset from the cutting channel to permit suturing of the tissue immediately adjacent a cut formed along the cutting channel. Cutting channel 136 in jaw 20 extends from a proximal end of inner surface 75 to slotted opening 82 and is laterally aligned with cutting channel 134 such that, when jaws 18 and 20 are closed, the two cutting channels cooperate to define a substantially rectangular passage between the jaws along which a cutting member can be advanced.

When incorporating the modification shown in FIG. 14, the instrument 10 according to the present invention will function as a tissue clamping and suturing unit and can be combined or coupled with various operating units carrying cutting members or other operating members to permit additional operative steps or functions to be performed. In FIG. 15, for example, the instrument of FIG. 14 is shown mated with an operating unit 138 including a hub 140 releasably coupled with the housing 12 and carrying an inner member 142 at least partly telescopically fitted within the intermediate tubular member 16. Hub 140 for operating unit 138 is generally rectangular with front and rear end walls 144 and 146, a top wall 148 and a bottom wall 150. Top and bottom walls of the hub are joined by lateral sidewalls (not shown) and front wall 144 includes a cylindrical protrusion 152 on an exterior face, the cylindrical protrusion having a configuration to mate with the cylindrical recess 64 formed in housing 12. Inner member 142 includes a cylindrical or tubular shaft 154 and an operating member in the form of a flat cutting blade 156 mounted at a distal end of the tubular shaft 154. The blade 156 has a width w slightly less than the diameter of the tubular shaft 154, a length 1 approximately equal to or greater than the length of the cutting channels 134 and 136 in jaws 18 and 20, and a thickness suitable for sliding within the cutting channels. The distal end of the inner member 142 is shown carrying a blade 156 but can carry any kind of operating member described in prior U.S. patent application Ser. No. 08/138,186, filed Jan. 20, 1995, the disclosure of which is incorporated herein by reference. The blade shown has a straight cutting edge 158 oriented perpendicularly relative to the longitudinal axis of the instrument; however, slanted, curved, serrated or toothed cutting edges could also be used. Blade 156 extends diametrically across the open distal end of tubular shaft 154 leaving openings on either side of the blade for communicating with the central passage formed by the tubular shaft. Tubular shaft 154 is telescopically fitted within the tubular portion of intermediate member 16 and extends through aligned openings in the front and rear walls 28 and 30 of housing 12 and the front and rear walls 144 and 146 of hub 140 to terminate proximally outside the hub at a spherical valve housing 160 with a proximal aperture 162 and a spherical valve member with an opening (not shown) disposed within the valve housing and connected with a knob 164 to control passage of instruments and/or fluids through the aperture and into the tubular shaft of the inner member.

A handle 166 extends transversely from tubular shaft 154 near the proximal end of the shaft and is angled distally to form a finger rest. An insulated connector 168 enters the tubular shaft 154 on a side opposite the handle and is connected with electrically conductive elements of the instrument for performing unipolar or bipolar electric coagulation, for example using the blade 156 as a conductive element. Tubular shaft 154 also carries a transverse flange 170 disposed within hub 140 between front and rear walls 144 and 146 of the hub. A bias member 172, shown as a helical coil spring, is disposed around the tubular shaft 154 and held in compression between the front wall 144 and the inner member flange 170 to bias the inner member 142 proximally within hub 140.

Figure 16:
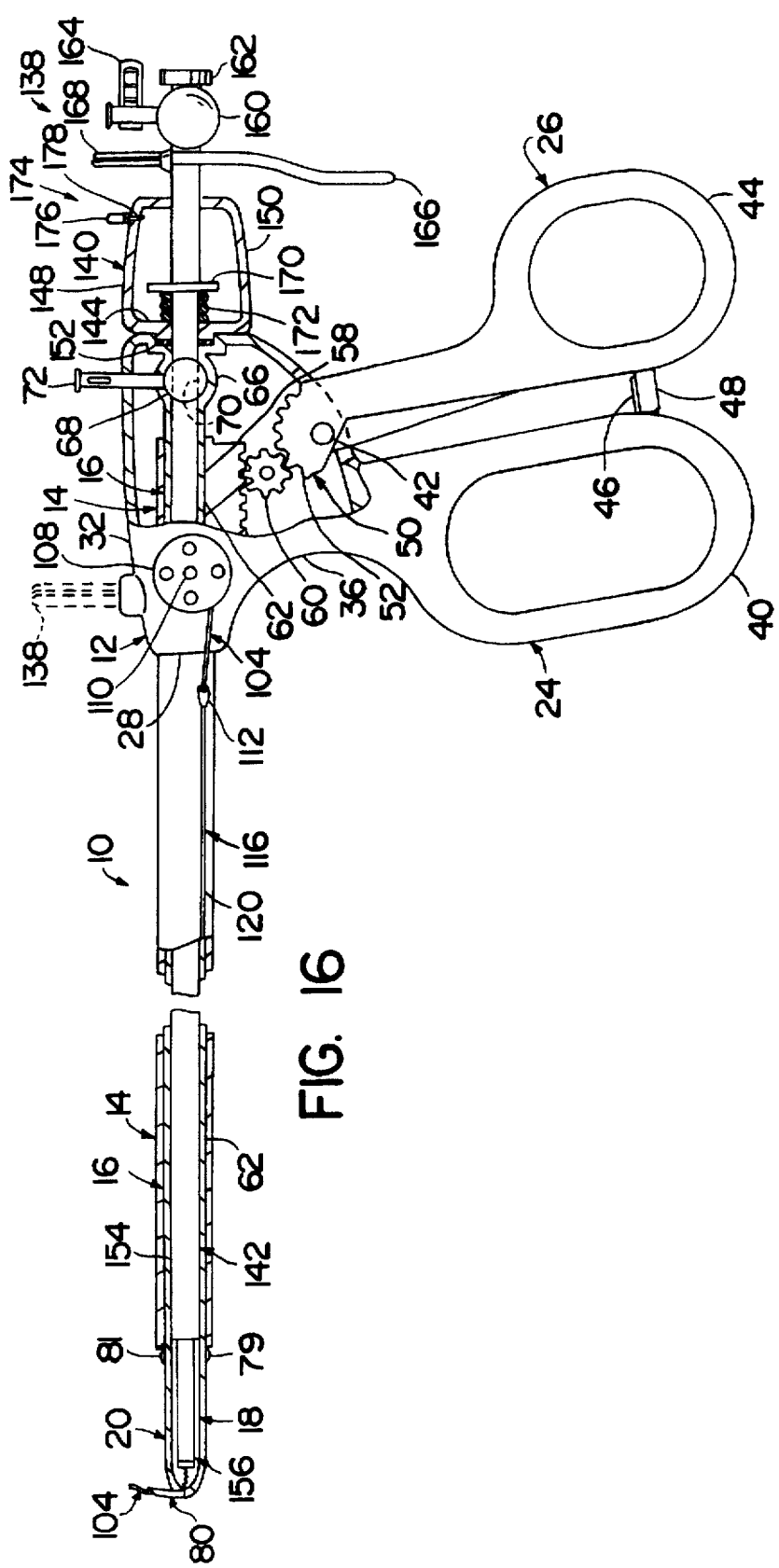
FIG. 16 is a broken side view, in elevation, illustrating use of the operating unit of FIG. 15 to cut tissue clamped between jaws of the combined tissue clamping and suturing instrument of FIG. 14.

Inner tubular member 142 is prevented from being inadvertently moved in a distal direction by a safety mechanism 174 disposed within the hub 140. A rotatable lever safety mechanism is shown whereby the inner tubular member 142 can be locked in a retracted position with the inner member flange 170 abutting the rear wall 146 by pivoting the lever into engagement with the flange and can subsequently be released prior to being moved distally by pivoting the lever out of engagement with the flange as shown in FIG. 16. It will be appreciated, however, that other safety mechanisms can be used, including, but not limited to, push-button locking and releasing safety mechanisms as shown and described in prior U.S. patent application Ser. No. 08/138, 186, filed Jan. 20, 1995, as well as levers, detents, and splined collars for example. Lever 176 extends through the top wall of the hub and is pivotally mounted on a pin 178 secured to the hub near the rear end wall for rotation about a central portion of the lever. A lower end of the lever 176 extends a suitable distance into the hub for engaging the inner member flange 170 in a retracted position to lock the inner member from distal movement.

The endoscopic instrument 10 can be provided as shown in FIG. 15 with the operating unit hub 140 attached to the combined tissue clamping and suturing unit housing 12, or the operating unit 138 can be provided separately so that the hub 140 can be fitted or mated with the housing 12 by the user. The latter is particularly desirable where a number of operating unit hubs carrying various types of inner members are available, allowing the user to select an appropriate hub/inner member combination for the particular procedure to be performed.

If the operating unit 138 is provided separately, assembly of the instrument 10 requires that valve handle 72 be turned approximately 90° from the closed position shown in FIG. 1 to the open position shown in FIG. 15 wherein the aperture 70 is aligned with the longitudinal axis of the instrument to permit passage of the operating unit through the central channel formed by intermediate member 16. Inner member 142 carried by the hub 140 can then be inserted through the opening in the rear wall 30 of the housing 12 and advanced distally into intermediate member 16 until the cylindrical projection 152 on the front wall 144 of the hub meets the cylindrical recess 64 formed in the rear wall 30 of the housing. Bias member 172 urges the inner member proximally toward the retracted position where the inner member flange 170 abuts the hub rear wall 146 causing blade 156 carried by inner member 142 to be disposed proximally of jaws 18 and 20. As mentioned previously, the inner member 142 can be locked in the retracted position and prevented from being moved distally by use of safety mechanism 174 such that blade 156 carried by the inner member cannot be inadvertently advanced toward the jaws.

The instrument shown in FIGS. 14 and 15 can be used in the manner described above to clamp anatomical tissue and place sutures without the need of having to use separate tissue clamping and suturing instruments. In addition, however, the modifications of FIGS. 14 and 15 allow the instrument to be used to clamp, suture and cut tissue without the need of having to use separate instruments to perform those functions. Anatomical tissue to be sutured is first clamped between jaws 18 and 20 of the instrument in the manner described above to immobilize the tissue and prevent bleeding. If engaged, safety lever 176 is disengaged as shown in FIG. 16 by rotating or pivoting the lever until a lower end of the lever is radially spaced from the flange to allow unobstructed passage of the flange past the lever. The inner member 142 is then advanced distally against the proximal bias of spring 172 by exerting a distal force on operating unit handle 166 until the handle abuts the rear wall of the hub or the bias member is completely compressed. Blade 156 at the distal end of inner member 142 is laterally aligned with cutting channels 134 and 136 such that, upon distal movement of inner member 142, blade 156 will advance distally along cutting channels 134 and 136 thereby cutting the anatomical tissue clamped between the jaws. Once cut, the anatomical tissue can be sutured in the manner previously described using a length of suture material 104 removed from the needle while simultaneously opening the jaws of the instrument.

Replacement of operating unit 138 involves withdrawing the hub 140 from the housing 12 along with the inner member 142 to permit a new operating unit hub carrying a different type of inner member to be inserted for performing other functions including, but not limited to, cutting, grasping, hooking, manipulating, dissecting, collecting tissue for biopsy, penetrating, injecting, creating suction, aspirating, irrigating, cauterizing, suturing, ligating, visualizing and illuminating. During substitution of operating units, the opening in the rear wall of the housing can be closed using a finger or conventional valves, such as flapper or trumpet valves, to help prevent loss of pneumoperitoneum. The tissue clamping and suturing instrument 10 can also be utilized alone, that is, without an operating unit; and, when used alone, the instrument can be sealed by rotating valve handle 72 to the closed position shown in FIG. 1 wherein the opening in the valve member 68 is oriented transverse to a longitudinal axis of the instrument and, thus, blocked to prevent loss of pneumoperitoneum.

Under certain circumstances, it may be desirable to mount the suture needle at locations other than at the tip of the jaw. For example, in FIGS. 17 and 18, a modification of the surgical instrument is shown wherein the suture needle 80 is proximally spaced a short distance from the tip 128 of jaw 18. Slotted opening 82 in jaw 20 is aligned with needle 80 and elongated slightly such that the needle will protrude from the slotted opening when the jaws are closed as shown in FIG. 18. A length of suture material 104 extends from peripheral groove 128 in the outer surface of the jaw to needle 80 through a groove extension 180 formed along the inner surface 74 of jaw 18 in alignment with a longitudinal axis of the jaw. Groove extension 180 extends from the edge of the jaw, that is, from the junction of inner and outer surfaces of the jaw, to the needle 80, and the groove extension has a cross-sectional configuration the same as or similar to that of groove 116. It will be appreciated that use of the instrument 10 shown in FIGS. 17 and 18 will proceed essentially the same as described above and that the needle can be proximally spaced from the tip of the jaw any amount dependent upon procedural use, can be laterally spaced from the position shown and/or placed next to a cutting channel as desired.

Any number of suture needles can be mounted on the jaw of the surgical instrument dependent upon the procedure to be performed. For example, in FIGS. 19 and 20, a modification of the instrument 10 is shown wherein a pair of laterally spaced suture needles 80 are mounted at the tip of jaw 18 on opposite sides of longitudinal cutting channels 134 and 136 formed along inner surfaces 74 and 75 of jaws 18 and 20, respectively. Each of the needles communicates with a groove 86 formed along the outer surface or periphery of jaw 18 so that separate lengths of suture material (not shown) supplied from opposite sides of the instrument can be carried by the needles in the manner described above. The cutting channels are laterally aligned with one another in opposed relation such that, when jaws 18 and 20 are closed, the cutting member 156, such as a blade or scissors, can be movably disposed within the cutting channels and operated as described above.

Figure 21:
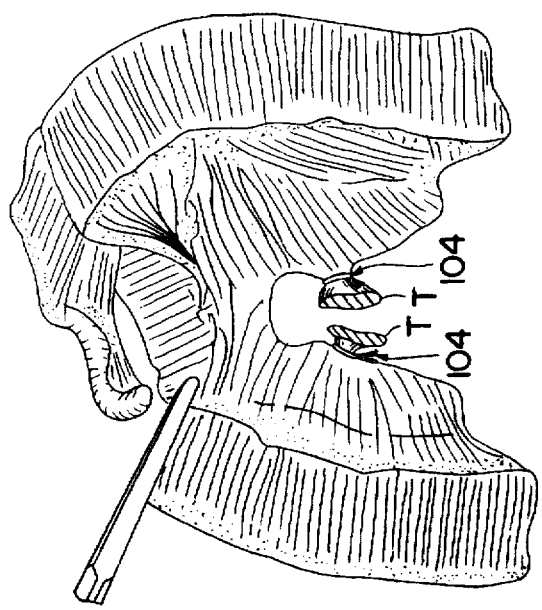
FIGS. 21–23 are fragmentary perspective views illustrating use of the combined tissue clamping and suturing instrument of FIGS. 19 and 20 for tissue clamping and suturing.
Figure 22:
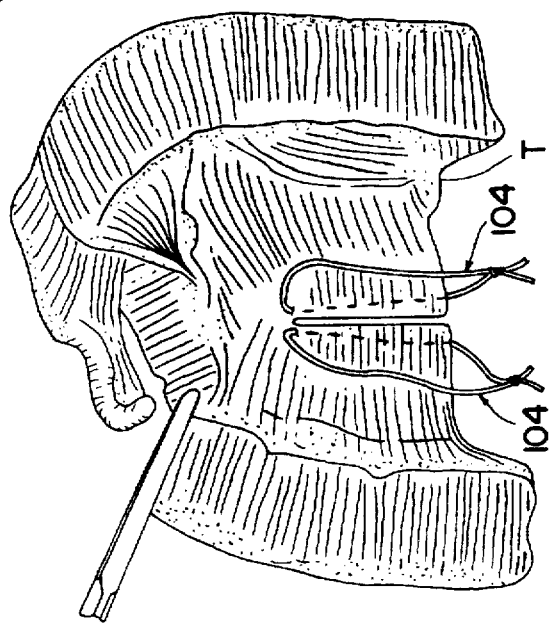
Figure 23:
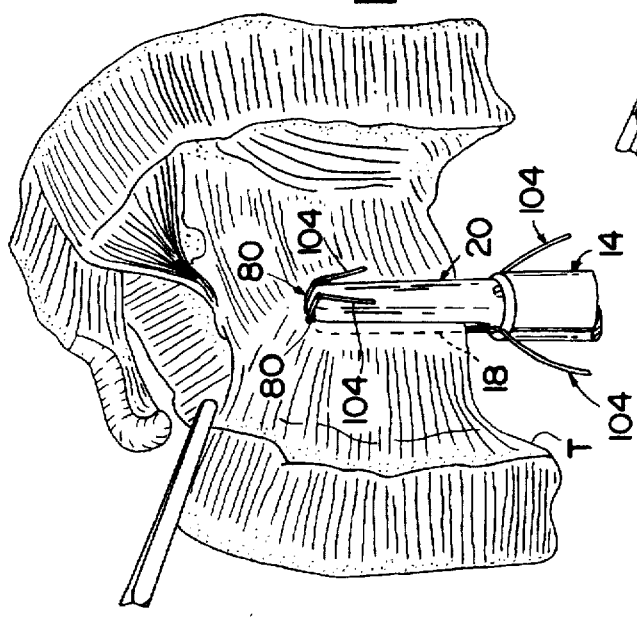

The modified instrument shown in FIGS. 19 and 20 can be used in a similar manner as described above in connection with the modifications of FIGS. 14 and 15. For example, in FIGS. 21–23, use of the modified tissue clamping and suturing instrument for resecting a portion of the bowel is shown. In FIG. 21, jaws 18 and 20 have been placed on opposite sides of the tissue T to be cut and have been clamped together by closing the jaws. At the same time, laterally spaced needles 80 have been made to penetrate through the tissue and to protrude from slotted openings 82 in jaw 20. With tissue T held between the jaws, cutting member 156 is advanced distally along the cutting channels to cut the tissue clamped between the jaws. Before, during or after the cutting procedure, opposite ends of the suture material are grasped and tugged in opposite directions to release the suture material from needles 80, the individual lengths of suture material thereby released being moved to opposite sides of the jaw as shown in FIG. 22 and tied in any conventional manner to gather the divided tissue as shown in FIG. 23. In addition to reducing the number of instruments needed to clamp, cut and suture tissue, it will be appreciated that the modifications of FIGS. 19 and 20 permit the suture material to be secured immediately adjacent both sides of the cut made in the tissue thereby minimizing the size of the residual tissue stump on both sides or, in other words, the amount of tissue overhanging the sutures. This is particularly advantageous when tissue on opposite sides of a cut are to remain within the body.

Another modification of the combined tissue clamping and suturing instrument of the present invention is illustrated in FIGS. 24 and 25 wherein a suture needle 80 is proximally spaced from the tip 127 of jaw 18 with slot 106 formed on a lateral side of the needle and slotted opening 82 formed in jaw 20 perpendicular to a longitudinal axis of the instrument. The slotted opening 82 extends from a lateral edge of the outer surface of the jaw in a transverse direction relative to a longitudinal axis of the instrument to be aligned with the needle such that, when the jaws are closed, the needle will protrude from the slotted opening as shown in FIG. 25. Groove 124 formed in jaw 18 extends longitudinally along the outer surface of jaw 18 and turns upward, toward inner surface 74 of the jaw, at a bend 126 longitudinally aligned with slot 106 in the needle. The groove connects with a groove extension 180 at an edge of the inner surface, the groove extension extending transversely from the groove across the inner surface to communicate with the interior of needle 80.

In addition to the above, FIG. 24 illustrates a second needle, shown by dotted lines at 80', mounted on jaw 18 in opposed relation to a transversely slotted opening, shown by dotted lines at 82', wherein the first and second needles 80 and 80' are longitudinally spaced in opposed relation to the slotted openings 82 and 82' to facilitate certain suturing procedures. Also shown is a modification of inner surface 74 wherein the surface is formed of a repeated pattern of diamond-shaped protrusions 76.

Figure 26:
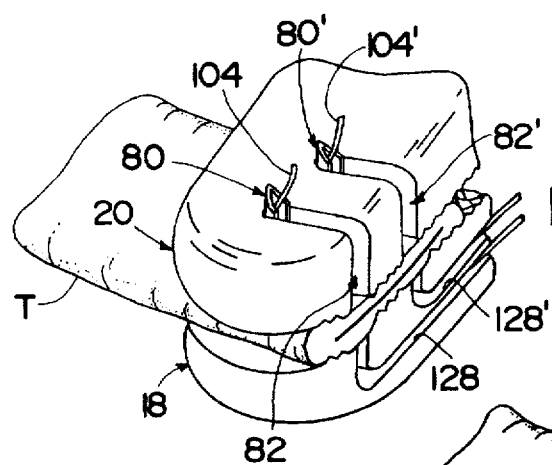
FIGS. 26 and 27 are fragmentary perspective views illustrating use of the combined tissue clamping and suturing instrument of FIGS. 24 and 25 for tissue clamping and suturing.
Figure 27:
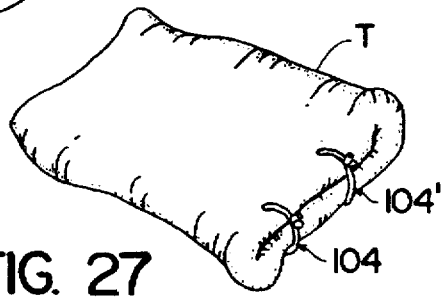

Use of the instrument of FIGS. 24 and 25 in closing-off a tubular vessel or organ is illustrated in FIGS. 26 and 27 wherein jaws 18 and 20 are positioned on opposite sides of a tubular vessel or organ T immediately adjacent a free end of the tubular vessel or organ and are closed in the manner described above to clamp the tissue between the jaws and cause needles 80 and 80' to protrude from slotted openings 82 and 82'. Slots 106 and 106' and slotted openings 82 and 82' are oriented toward the free end of the tubular vessel or organ permitting suture material 104 and 104' to be drawn directly out of the needles 80 and 80' and tied around the free end as shown in FIG. 27 to form stitches closing the tubular vessel or organ.

Figure 28:
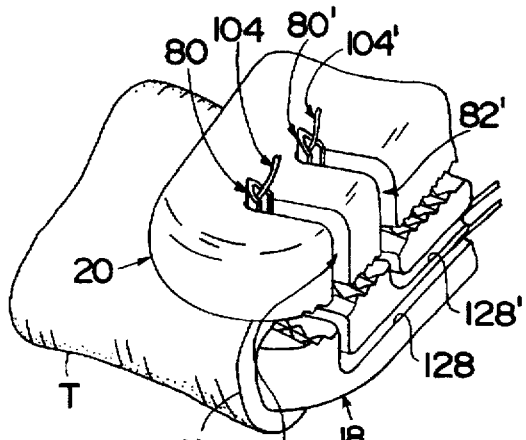
FIG. 28 is a fragmentary perspective view illustrating use of the combined tissue clamping and suturing instrument of FIGS. 24 and 25 to place lengths of suture material in the wall of a tubular vessel or organ.

The instrument of FIGS. 24 and 25 can also be used in the manner shown in FIG. 28 to place lengths of suture material in the walls of a tubular vessel or organ T by positioning jaw 18 within the tubular vessel or organ and jaw 20 on a side of a tubular wall W opposite jaw 18. The jaws are then closed to cause needles 80 and 80' to penetrate through the tubular wall. Lengths of suture material 104 and 104' are carried with the needles, and the free ends of the suture material can, for example, be used in manipulating the tubular vessel or organ and/or performing anastomosis.

It will be appreciated that the combined tissue clamping and suturing instrument of FIG. 24 can also be used in a manner similar to that described above in connection with FIGS. 10–13 when it is desired to clamp anatomical tissue between the jaws, cut alongside the jaws and suture the tissue. Also, the instruments of FIGS. 1, 14, 17 and 19 can be used in a similar manner to that described above in connection with FIGS. 26–28.

Figure 29:
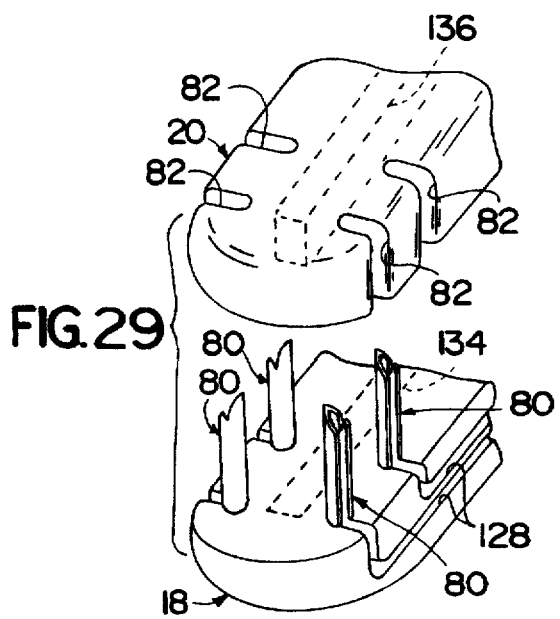
FIGS. 29 and 30 are fragmentary perspective views of an additional modification of the combined tissue clamping and suturing instrument according to the present invention.
Figure 30:
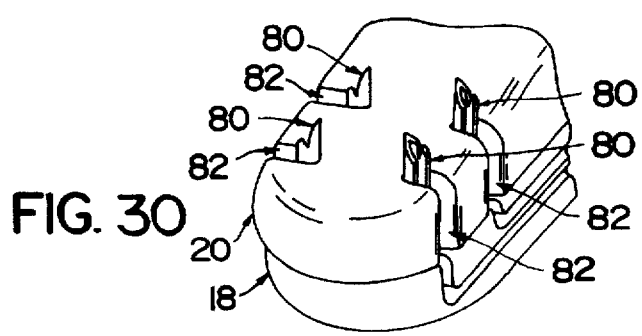

The instrument shown in FIGS. 29 and 30 is similar to those previously described but with two pairs of longitudinally spaced needles 80 mounted on jaw 18 in opposed relation to transversely slotted openings 82 formed in jaw 20. The needles 80 are arranged in two laterally spaced rows with grooves 116 being formed on lateral sides of the outer surface or periphery of jaw 18 in communication with groove extensions 180 leading to each needle. Use of the modified surgical instrument shown in FIGS. 29 and 30 is similar to that described and shown for the instruments of FIGS. 1, 14, 17 and 19.

From the above, it will be appreciated that the surgical instrument of the present invention permits various types of sutures to be formed without the need of having to use multiple tissue clamping and needle holding instruments. By "sutures" is meant lengths of suture material secured to anatomical tissue including, but not limited to, ligatures, ties or stitches formed of lengths of suture material. The lengths of suture material are attached to or carried by one or more suture needles mounted on at least one of two clamping jaws of the instrument, the suture material being removable therefrom when the jaws are closed so that the sutures can be set simultaneously with opening of the jaws if desired.

The needles can be straight or curved, rigid or flexible, and are preferably hollow and slotted with the point or tip of each needle being honed to a desired shape and configuration to form, for example, cutting points for hard to penetrate tissue such as skin and tendon, taper points for use in soft tissue such as intestine and peritoneum, or blunt points for use in suturing friable tissue. While it is preferred that the needles be hollow and slotted to reduce penetration resistance and the possibility of the suture material becoming snagged on other instruments or tissue, it is also possible to form the surgical instrument with solid needles and to attach lengths of suture material near the tips of the needles via slots or eyes, for example. The body or shaft of each needle can have any configuration in cross-section including, but not limited to, round, oval, flat and triangular cross-sectional configurations. Further, any of the needles described above can be coated to enhance smooth passage through the anatomical tissue being sutured. The gage or diameter and length of the body or shaft of each needle will vary depending upon the toughness of the tissue to be sutured and the depth of penetration desired. If an opening is formed in a jaw in opposed relation to a suture needle, the body of the needle should be sufficiently long to cause the point of the needle to protrude from the opening beyond an outer surface of the jaw when the jaws are clamped around anatomical tissue being sutured. The needles can be permanently affixed to a jaw to be sterilized or disposed of with the rest of the instrument or the needles can be removable for disposal or sterilization as desired. If removable, the needles can be coupled with the jaw using any suitable method such as, for example, friction fit, controlled release, threaded engagement or detents.

When an opening is formed in a jaw opposite a suture needle carried by an opposed jaw, the opening will preferably extend through the jaw and have a shape to receive the needle and communicate with an edge of the jaw. While slotted openings have been shown and described, other shapes can be used including polygonal and elliptical openings that communicate with an edge of the jaw.

The jaws making up the jaw portion of the combined tissue clamping and suturing instrument can be formed as an integral one-piece unit or assembled from separate pieces; and, depending on procedural use, one of the jaws can be fixed and the other movable, both jaws can be movable, the jaws can be linked by pivots or formed at the end of a tubular member or formed at the end of a pair of pivotally connected arms. The jaws can be straight, curved and/or angled and can have inner, tissue-engaging surfaces or faces for grasping and clamping anatomical tissue and/or objects such as needles. Any of the jaws shown or described herein can be formed with inner surfaces formed of repeated patterns of diamond-shaped protrusions, lateral and/or longitudinal ribs and/or other types of textured patterns suitable for clamping tissue to be sutured. One or both of the jaws can be formed with cutting members mounted on the jaws and/or with cutting channels formed in the jaws for accommodating movable cutting members such as, for example, blades and scissors that are advanced along the channels and/or operated by opening and closing the jaws. Examples of cutting members that can be used with the instrument of the present invention include any of the operating or cutting members shown in prior U.S. patent application Ser. No. 08/138,186, filed Jan. 20, 1995, the disclosure of which is incorporated herein by reference. The cutting channels can extend part way along the jaw to form stops or abutments limiting distal movement of the cutting members or can extend the complete length of a jaw to form openings or apertures at a distal end or tip of the jaw to allow passage of the cutting member beyond the tip of the jaw, e.g., to trim free ends of the suture material applied to tissue. When a cutting channel is formed between jaws of the instrument, one or more suture needles can be mounted along one side of the channel, on opposite sides of the channel (as shown in FIG. 19) or at the distal end of the channel. When the instrument is to be provided with cutting members, tissue positioned between the jaws can be cut simultaneously with clamping of the tissue (e.g., by use of scissors disposed within the cutting channels or cutting members mounted directly on the jaws) or the tissue can be cut subsequent to clamping (e.g., by advancing a blade along the cutting channels). The jaws can have any shape in cross-section when closed, including circular, elliptical, rectangular and polygonal configurations, and can have opposed arcuate or concave portions for holding tubular objects without compressing the objects and removable jaw inserts if desired.

Lengths of suture material are preferably attached near the point or tip of each needle to be easily grasped when extended through an opening in an opposed jaw. If the needles are hollow and slotted, the suture material is preferably passed through the needles to assure smooth penetration of anatomical tissue by the needle with minimum resistance and tissue trauma, the presence of the suture material at the open beveled end of the needle also helping to prevent coring of the tissue. If desired, the portion of the suture material overhanging the notch at the beveled end of the needle can be trimmed prior to penetrating anatomical tissue to further reduce tissue resistance. Upon penetrating through the tissue, the suture material can be advanced through the needle manually or by use of a feed mechanism to extend a suitable length for being grasped. Grooves can also be formed along the outer surfaces or sides of the jaws in communication with the hollow needles to serve as passages through which the suture material may extend and to prevent loose lengths of suture material from becoming snagged on other instruments or contaminating adjacent tissue structures or organs. By "outer surfaces" of the jaws are meant the surfaces not engaging anatomical tissue; however, grooves or groove extensions can also be formed in the inner, tissue-clamping surfaces of the jaws when necessary to communicate with needles spaced from edges of the jaws. A single groove can also be extended around the entire periphery of a jaw (as shown in FIGS. 4 and 5) and connected with a needle via an extension, if necessary, so that a length of suture material can be extended along either lateral side of the instrument into the needle depending upon which side of the instrument the suture is to be applied.

When the body of a hollow needle is slotted to permit removal of a length of suture material from within the needle, the slot can be straight or curved and of uniform or varying width as desired.

Any number of suture needles can be mounted on one or both jaws of the surgical instrument; and, while one or two needles in spaced relation have been shown mounted on a single jaw, it will be appreciated that greater than two needles can be mounted on a jaw in spaced relation, depending upon the length of the tissue to be sutured and the desired spacing between sutures. When multiple needles are mounted on a jaw of the instrument, the needles can be attached to free lengths of suture material, can be fed from a single spool carrying multiple lengths of suture material, or can be fed from spools on opposite sides of the instrument such that lengths of suture material run along grooves on both sides of a jaw. Further, when spools are mounted on opposite sides of the instrument, lengths of suture material can be crossed at the tip of the jaw or elsewhere and then attached to respective needles so as to form cross-stitches or ligatures when tied or set. Whether fed from spools or provided as free lengths, the lengths of suture material can also be provided with knotting elements to assist in setting the sutures. Examples of knotting elements suitable for use with the present invention include those shown and described in prior U.S. patent applications Ser. No. 08/366, 285, filed Dec. 29, 1994; Ser. No. 08/377,723, filed Jan. 25, 1995; Ser. No. 08/401,002, filed Mar. 9, 1995; and Ser. No. 08/531,153, entitled "Ligating Instrument With Multiple Loop Ligature Supply and Methods Therefor," filed Sep. 15, 1995, the disclosures of which are incorporated herein by reference.

The handle portion of the combined tissue clamping and suturing instrument shown and described herein is exemplary of the types of conventional handle mechanisms suitable for performing the function of actuating the jaws; accordingly, the handles can have any configuration to actuate the jaws including, but not limited to, configurations employing a pair of pivotally connected arms, one fixed and one pivoted arm, a pistol grip with a movable trigger, or resilient U-shaped members. Further, the handle portion of the instrument can be configured to rotate relative to a longitudinal axis of the instrument so that, for example, in one position, the handles will extend laterally from the instrument or at a substantially perpendicular angle relative to the longitudinal axis; while, in another position, the handles will extend proximally from the instrument like scissors handles.

It will be appreciated that the handle portion and jaw portion of the combined tissue clamping and suturing instrument can be integrally formed as a one-piece unit or formed as separate components and coupled together, for example, by use of pivots, linkages, rods, cables, telescoping members, brackets and other mechanical and/or electrical couplings.

When the instrument is formed of telescoping members, it will also be appreciated that individual tubular members, such as the intermediate member, can be made rotatable about a longitudinal axis of the instrument either alone or in combination with other telescoping members. Moreover, when the instrument is coupled with an operating unit, the instrument housing and operating unit can have any configuration for being releasably coupled including, but not limited to, threaded or telescoping portions, detents, latches or any other suitable connection. Furthermore, the housing and hub can be cylindrical or rectangular as shown or have any other useful or convenient configuration in cross-section.

When the instrument is provided with a spool, the spool can be mounted on the housing or on any other portion of the instrument such as, for example, the outer tubular member as shown by dotted lines in FIG. 2 at 108'.

The components of the surgical instrument of the present invention can be made of any suitable, medical grade materials to permit sterilization for re-use or for single patient use. The components can be made of multiple parts of various configurations and materials to reduce cost.

The features of the various embodiments described above can be combined in any manner desired dependent upon the operational requirements of the procedure to be performed and the complexity of the surgical instrument.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A combined tissue clamping and suturing instrument comprising a handle portion;
   a jaw portion selectively actuated by operation of said handle portion, said jaw portion including a pair of opposed jaws;
   a hollow suture needle mounted on a first of said jaws, said hollow suture needle having a first open end mounted on said first jaw and a second open end adjacent a tissue penetrating point said first and second open ends being connected by a slot formed in said hollow needle; and
   a length of suture material extending through said hollow needle;
   wherein said slot has a width preventing said length of suture material from falling out of said hollow suture needle in a direction transverse to a longitudinal axis of said needle while permitting said length of suture material to be removed from said hollow suture needle when urged in a direction transverse to said needle longitudinal axis.

2. A combined tissue clamping and suturing instrument as recited in claim 1 wherein each jaw includes an outer surface and an inner, tissue-engaging surface, a groove being formed on said outer surface of said first jaw and a portion of said suture material being disposed within said groove.

3. A combined tissue clamping and suturing instrument as recited in claim 2 wherein said groove communicates with said first open end of said hollow needle body.

4. A combined tissue clamping and suturing instrument as recited in claim 3 wherein said suture needle slot has a width smaller than a diameter of said length of suture material to prevent said suture material from falling out of said hollow suture needle.

5. A combined tissue clamping and suturing instrument as recited in claim 4 wherein said groove decreases in width toward said outer surface of said first jaw to define an elongate slot along said outer surface of said first jaw, said elongate slot having a width smaller than a diameter of said length of suture material to prevent said suture material from falling out of said groove.

6. A combined tissue clamping and suturing instrument as recited in claim 5 wherein said hollow needle body and said groove are of substantially circular cross-section.

7. A combined tissue clamping and suturing instrument as recited in claim 2 and further comprising a spool disposed proximally of said groove, said length of suture material being dispensed from said spool.

8. A combined tissue clamping and suturing instrument as recited in claim 1 wherein an opening is formed through a second of said jaws opposite said hollow suture needle, said opening extending inwardly from an edge of said second jaw to receive said hollow suture needle when said jaws are closed and to permit removal of said length of suture material from said closed jaws in a direction transverse to said needle longitudinal axis using said slot in said hollow suture needle and said opening in said second jaw.

9. A combined tissue clamping and suturing instrument as recited in claim 8 wherein said needle has a length to cause said second open end of said needle to protrude from said second jaw opening when said jaws are closed.

10. A combined tissue clamping and suturing instrument as recited in claim 9 wherein said opening is an elongate slotted opening communicating with a peripheral edge of said second jaw.

11. A combined tissue clamping and suturing instrument as recited in claim 10 wherein said elongate opening extends longitudinally.

12. A combined tissue clamping and suturing instrument as recited in claim 11 wherein said suture needle is proximally spaced from a distal tip of said first jaw.

13. A combined tissue clamping and suturing instrument comprising
   a handle portion;
   a jaw portion selectively actuated by operation of said handle portion, said jaw portion including a pair of opposed jaws;
   a hollow suture needle mounted on a first of said jaws, said hollow needle having a first open end mounted on said first jaw and a second open end defining a tissue penetrating point, said first and second open ends being connected by a slot formed in said hollow needle: and
   a length of suture material extending through said hollow needle;
   wherein a notch is formed adjacent said point of said hollow suture needle and said length of suture material is held within said notch.

14. A combined tissue clamping and suturing instrument as recited in claim 13 wherein said second open end is beveled to produce edges converging at said needle point and wherein said notch is formed along one of said bevel edges.

15. A combined tissue clamping and suturing instrument as recited in claim 14 wherein said notch is V-shaped.

16. A combined tissue clamping and suturing instrument comprising
   a handle portion;
   a jaw portion selectively actuated by operation of said handle portion, said jaw portion including a pair of opposed jaws;
   a suture needle extending from a first of said jaws to a tissue penetrating point;
   a length of suture material extending along said suture needle and being coupled therewith to be removable therefrom in a transverse direction relative to a longitudinal axis of said needle; and an elongate slotted opening formed through a second of said jaws opposite said suture needle and communicating with an edge of said second jaw such that, when said jaws are closed, said suture needle will be received within said opening and said length of suture material will be removable from said closed jaws in a direction transverse to said needle longitudinal axis using said opening in said second jaw;

wherein said suture needle is proximally spaced from a distal tip of said first jaw and said elongate opening extends laterally from an edge of said second jaw transverse to a longitudinal axis of said second jaw.

17. A combined tissue clamping and suturing instrument comprising a handle portion;

a jaw portion selectively actuated by operation of said handle portion, said jaw portion including a pair of opposed jaws, wherein said jaws define a tissue receiving space therebetween and wherein a longitudinal cutting channel is formed in a first of said jaws;

a cutting member movably disposed along said longitudinal cutting channel and including a distal-facing cutting edge extending into said tissue receiving space between said jaws to cut anatomical tissue disposed between said jaws when said cutting member is longitudinally moved;

a suture needle extending from said first jaw to a tissue penetrating point; and a length of suture material carried by said suture needle.

18. A combined tissue clamping and suturing instrument as recited in claim 17 wherein said suture needle is hollow and said suture material extends through said needle.

19. A combined tissue clamping and suturing instrument as recited in claim 18 wherein a slot is formed in said hollow suture needle in communication with open ends of said needle.

20. A combined tissue clamping and suturing instrument comprising a handle portion:

a jaw portion selectively actuated by operation of said handle portion, said jaw portion including a pair of opposed jaws, wherein a longitudinal cutting channel is formed in a first of said jaws;

a cutting member movably disposed along said longitudinal cutting channel and having a cutting edge extending between said jaws to cut anatomical tissue when said cutting member is moved;

a suture needle extending from said first jaw to a tissue penetrating point; and a length of suture material carried by said suture needle;

wherein said suture needle is laterally offset from said longitudinal cutting channel.

21. A combined tissue clamping and suturing instrument comprising a handle portion;

a jaw portion selectively actuated by operation of said handle portion, said jaw portion including a pair of opposed jaws;

a plurality of suture needles spaced longitudinally along a first of said jaws, each of said needles extending from said first jaw to a tissue penetrating point;

plural lengths of suture material, each of said lengths extending along a respective suture needle and coupled therewith to be removable therefrom in a transverse direction relative to a longitudinal axis of said suture needle; and opening means extending inwardly from an edge of a second of said jaws for receiving at least one of said suture needles when said jaws are closed and for permitting removal of a corresponding length of suture material from said at least one suture needle in a transverse direction relative to said needle longitudinal axis when said jaws are closed so that said length of suture material can be removed from said closed jaws and tied while simultaneously opening said jaws.

22. A combined tissue clamping and suturing instrument as recited in claim 21 and further comprising a plurality of openings formed in said second jaw in opposed relation to said plurality of hollow needles, said openings each extending inwardly from an edge of said second jaw and being aligned with a hollow suture needle such that, when said jaws are closed, said hollow suture needles will be received within said openings and said lengths of suture material can be removed from said closed jaws in a transverse direction relative to said longitudinal axis of said needles.

23. A combined tissue clamping and suturing instrument comprising a handle portion:

a jaw portion selectively actuated by operation of said handle portion, said jaw portion including a pair of opposed jaws:

a plurality of suture needles spaced longitudinally along a first of said jaws, each of said needles extending from said first jaw to a tissue penetrating point:

plural lengths of suture material, each of said lengths extending along a respective suture needle and being removable therefrom in a transverse direction relative to a longitudinal axis of said suture needle: and an opening extending inwardly from an edge of a second of said jaws to receive at least one of said suture needles when said jaws are closed and to permit removal of a corresponding length of suture material from said at least one suture needle in a transverse direction relative to said needle longitudinal axis when said jaws are closed so that said length of suture material can be removed from said closed jaws and tied while simultaneously opening said jaws;

wherein each of said suture needles is hollow and axially opposed ends of each hollow suture needle are open and connected by a slot formed in said hollow suture needle, each length of suture material extending through one of said hollow suture needles;

wherein each of said slots has a width preventing said length of suture material from falling out of said hollow suture needle in a direction transverse to a longitudinal axis of said needle while permitting said length of suture material to be removed from said hollow suture needle when urged in a direction transverse to said needle longitudinal axis.

24. A combined tissue clamping and suturing instrument as recited in claim 23 wherein a plurality of grooves are formed in an outer surface of said first jaw to hold said lengths of suture material.

25. A combined tissue clamping and suturing instrument comprising a handle portion;

a jaw portion selectively actuated by operation of said handle portion, said jaw portion including a pair of opposed jaws;

a plurality of suture needles spaced laterally across a first of said jaws, each of said needles extending from said first jaw to a tissue penetrating point;

plural lengths of suture material, each of said lengths extending along a respective suture needle and coupled therewith to be removable therefrom in a lateral direction relative to a longitudinal axis of said suture needle; and opening means extending inwardly from an edge of a second of said jaws for receiving at least one of said suture needles when said jaws are closed and for permitting removal of a corresponding length of suture material from said at least one suture needle in a transverse direction relative to said needle longitudinal axis when said jaws are closed so that said length of suture material can be removed from said closed jaws and tied while simultaneously opening said jaws.

26. A combined tissue clamping and suturing instrument comprising a handle portion;

a jaw portion selectively actuated by operation of said handle portion, said jaw portion including a pair of opposed jaws;

a plurality of suture needles spaced laterally across a first of said jaws, each of said needles extending from said first jaw to a tissue penetrating point;

plural lengths of suture material, each of said lengths extending along a respective suture needle and being removable therefrom in a lateral direction relative to a longitudinal axis of said suture needle; and an opening extending inwardly from an edge of a second of said jaws to receive at least one of said suture needles when said jaws are closed and to permit removal of a corresponding length of suture material from said at least one suture needle in a transverse direction relative to said needle longitudinal axis when said jaws are closed so that said length of suture material can be removed from said closed jaws and tied while simultaneously opening said jaws;

wherein each of said suture needles is hollow and axially opposed ends of each hollow suture needle are open and connected by a slot formed in said hollow suture needle, each length of suture material extending through one of said hollow suture needles;

wherein each of said slots has a width preventing said length of suture material from falling out of said hollow suture needle in a direction transverse to a longitudinal axis of said needle while permitting said length of suture material to be removed from said hollow suture needle when urged in a direction transverse to said needle longitudinal axis.

27. A combined tissue clamping and suturing instrument as recited in claim 26 wherein a plurality of grooves are formed in an outer surface of said first jaw to hold said lengths of suture material.

28. A combined tissue clamping and suturing instrument as recited in claim 25 wherein said opening means includes a plurality of openings formed in said second jaw in opposed relation to said plurality of suture needles, said openings each extending inwardly from an edge of said second jaw and being aligned with a suture needle such that, when said jaws are closed, said suture needles will be received within said openings and said lengths of suture material can be removed from said closed jaws in a transverse direction relative to said longitudinal axes of said needles.

29. A combined tissue clamping and suturing instrument comprising a handle portion;

a jaw portion selectively actuated by operation of said handle portion, said jaw portion including a pair of opposed jaws;

a plurality of suture needles spaced laterally across a first of said jaws, each of said needles extending from said first jaw to a tissue penetrating point; and plural lengths of suture material, each of said lengths being carried by one of said suture needles;

wherein a longitudinal cutting channel is formed in said first jaw parallel with a longitudinal axis of said first jaw between a pair of laterally spaced suture needles and further comprising a cutting member movably disposed along said cutting channel and having a cutting edge extending between said jaws to cut anatomical tissue disposed between said jaws.

30. A method of suturing anatomical tissue using a combined tissue clamping and suturing instrument having a hollow, slotted suture needle mounted on one of a pair of opposed jaws, said method comprising the steps of positioning a length of suture material within the suture needle;

positioning the jaws around anatomical tissue to be sutured;

closing the jaws to clamp the anatomical tissue between tissue clamping surfaces of the jaws;

receiving the point of the suture needle within an opening extending inwardly from an edge of the opposed jaw;

removing the length of suture material from the closed jaws in a direction transverse to the needle longitudinal axis using the slot in the hollow suture needle and the opening in the opposed jaw; and forming a suture using the length of suture material while simultaneously opening the jaws to reduce clamping pressure on the anatomical tissue.

31. A method of suturing anatomical tissue as recited in claim 30 and further comprising the step of penetrating through the anatomical tissue using the suture needle.

32. A method of suturing anatomical tissue as recited in claim 30 and further comprising the step of advancing a blade with a cutting edge extending between the jaws along a channel formed in at least one of the jaws to cut the anatomical tissue clamped between the jaws.

33. A method of suturing anatomical tissue as recited in claim 30 wherein a pair of laterally spaced suture needles are mounted on one of the jaws and further comprising the steps of positioning lengths of suture material within the pair of laterally spaced suture needles and penetrating through the anatomical tissue using the pair of laterally spaced suture needles.

34. A method of suturing anatomical tissue as recited in claim 33 and further comprising the step of advancing a cutting member with a cutting edge extending between the jaws through the anatomical tissue between the pair of laterally spaced suture needles.

35. A method of suturing anatomical tissue as recited in claim 30 wherein a plurality of longitudinally spaced suture needles are mounted on one of the jaws and further comprising the steps of positioning lengths of suture material within the longitudinally spaced suture needles and penetrating through the anatomical tissue using the longitudinally spaced suture needles.

36. A method of suturing anatomical tissue as recited in claim 35 and further comprising, prior to said step of positioning said jaws around anatomical tissue, cutting the anatomical tissue to perform anastomosis.

37. A method of suturing anatomical tissue using a combined tissue clamping and suturing instrument having a suture needle mounted on one of a pair of opposed jaws, said method comprising the steps of attaching the length of suture material to the suture needle near a tissue penetrating point of the suture needle;

positioning the jaws around anatomical tissue to be sutured;

closing the jaws to clamp the anatomical tissue between tissue clamping surfaces of the jaws;

receiving the point of the suture needle within an opening extending inwardly from an edge of the opposed jaw;

advancing a blade with a cutting edge extending between the jaws along a channel formed in at least one of the jaws to cut the anatomical tissue clamped between the jaws;

removing the length of suture material from the suture needle and the closed jaws using the opening; and forming a suture using the length of suture material while simultaneously opening the jaws to reduce clamping pressure on the anatomical tissue.

38. A method of suturing anatomical tissue using a combined tissue clamping and suturing instrument having a pair of laterally spaced suture needles mounted on one of a pair of opposed jaws, said method comprising the steps of attaching lengths of suture material to the pair of laterally spaced suture needles;

positioning the jaws around anatomical tissue to be sutured;

closing the jaws to clamp the anatomical tissue between tissue clamping surfaces of the jaws;

penetrating through the anatomical tissue using the pair of laterally spaced suture needles;

receiving points of the suture needles within at least one opening extending inwardly from an edge of the opposed jaw;

removing the lengths of suture material from the suture needles and closed jaws using the at least one opening; and forming a suture using the length of suture material while simultaneously opening the jaws to reduce clamping pressure on the anatomical tissue.

39. A method of suturing anatomical tissue as recited in claim 38 and further comprising the step of advancing a cutting member through the anatomical tissue between the pair of laterally spaced suture needles.

40. A method of suturing anatomical tissue using a combined tissue clamping and suturing instrument having a plurality of longitudinally spaced suture needles mounted on one of a pair of opposed jaws, said method comprising the steps of attaching lengths of suture material to the longitudinally spaced suture needles;

positioning the jaws around anatomical tissue to be sutured;

closing the jaws to clamp the anatomical tissue between tissue clamping surfaces of the jaws;

penetrating through the anatomical tissue using the longitudinally spaced suture needles;

receiving points of the suture needles within at least one opening extending inwardly from an edge of the opposed jaw;

removing the lengths of suture material from the suture needles and the closed jaws using the at least one opening; and forming sutures using the lengths of suture material while simultaneously opening the jaws to reduce clamping pressure on the anatomical tissue.

41. A combined tissue clamping and suturing instrument comprising a handle portion;

a jaw portion selectively actuated by operation of said handle portion, said jaw portion including a pair of opposed jaws;

a hollow suture needle mounted on a first of said jaws, said hollow needle having a first open end mounted on said first jaw and a second open end with a peripheral edge defining a tissue penetrating point, said first and second open ends being connected by a slot formed in said hollow needle; and a length of suture material extending through said hollow needle, said length of suture material being of a size to be removable from said hollow suture needle in a direction transverse to a longitudinal axis of said needle using said slot.

42. A combined tissue clamping and suturing instrument comprising a handle portion;

a jaw portion selectively actuated by operation of said handle portion, said jaw portion including a pair of opposed jaws;

a substantially straight, hollow suture needle mounted on a first of said jaws, said hollow needle having a first open end mounted on said first jaw and a second open end adjacent a tissue penetrating point, said first and second open ends being connected by a slot formed in said hollow needle; and a length of suture material extending through said hollow needle, said length of suture material being of a size to be removable from said hollow suture needle in a direction transverse to a longitudinal axis of said needle using said slot.

43. A combined tissue clamping and suturing instrument comprising a handle portion;

a jaw portion selectively actuated by operation of said handle portion, said jaw portion including a pair of opposed jaws;

a suture needle extending from a first of said jaws toward a second of said jaws and terminating at a tissue penetrating point;

a groove formed on an outer surface of said first jaw; and a length of suture material extending through said groove and along said suture needle to be disposed adjacent said tissue penetrating point, said groove decreasing in width toward said outer surface of said first jaw to define a slot having a width preventing said length of suture material from falling out of said groove.

44. A combined tissue clamping and suturing instrument as recited in claim 43 wherein said width of said slot defined by said groove is such that said length of suture material can be removed from said groove by urging said suture material laterally through said slot by application of force.

* * * * *